United States Patent
Wong et al.

(10) Patent No.: US 11,124,833 B2
(45) Date of Patent: Sep. 21, 2021

(54) SALIVARY EXTRACELLULAR RNA BIOMARKERS FOR GINGIVITIS

(71) Applicants: The Regents of the University of California, Oakland, CA (US); Colgate-Palmolive Company, New York, NY (US)

(72) Inventors: David T. W. Wong, Beverly Hills, CA (US); Karolina Elzbieta Kaczor-Urbanowicz, Los Angeles, CA (US); Harsh Mahendra Trivedi, Hillsborough, NJ (US); James Masters, Ringoes, NJ (US)

(73) Assignee: Colgate-Palmolive Company, New York, NY (US)

( * ) Notice: Subject to any disclaimer, the term of this patent is extended or adjusted under 35 U.S.C. 154(b) by 11 days.

(21) Appl. No.: 16/171,418

(22) Filed: Oct. 26, 2018

(65) Prior Publication Data

US 2019/0127800 A1    May 2, 2019

Related U.S. Application Data

(60) Provisional application No. 62/577,887, filed on Oct. 27, 2017.

(51) Int. Cl.
*C12Q 1/6883* (2018.01)

(52) U.S. Cl.
CPC ..... *C12Q 1/6883* (2013.01); *C12Q 2600/106* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| | | |
|---|---|---|
| 8,753,820 B2 | 6/2014 | Trivedi et al. |
| 2003/0040009 A1 | 2/2003 | Denny |
| 2010/0210023 A1 | 8/2010 | Wong et al. |
| 2014/0335534 A1 | 11/2014 | Li et al. |

FOREIGN PATENT DOCUMENTS

| | | |
|---|---|---|
| WO | 2013/162100 | 10/2013 |
| WO | 2014/037924 | 3/2014 |

OTHER PUBLICATIONS

Zubakov et al. Int J Legal Med. 2008. 122: 135-142 (Year: 2008).*
Affymetrix: "Datasheet Affymetrix "GeneChip Human Transcriptome Array 2.0"", Jul. 23, 2013, retrieved from the Internet on Dec. 12, 2018: URL:http://tools.thermofisher.com/content/sfs/brochures/hta_array_2_0_datasheet.pdf.
Giannobile, W., et al., "Saliva as a diagnostic tool for periodontal disease: current state and future directions", Periodontology 2000, 50(1):52-64, 2009.
International Search Report and Written Opinion of the International Searching Authority issued on corresponding application No. PCT/US2018/057623 dated Feb. 14, 2019.
Kaczor-Urbanowicz, K., et al., "Salivary exRNA biomarkers to detect gingivitis and monitor disease regression", Journal of Clinical Periodontology, 45(7):806-817, 2018.
Kinney, J. S., et al. "Saliva/Pathogen Biomarker Signatures and Periodontal Disease Progression", Journal of Dental Research, 90(6):752-758, 2011.
Lee, C. H., et al., "Small proline-rich protein 1 is the major component of the cell envelope of normal human oral keratinocytes", FEBS LETT, 477(3):268-272, 2000.
Starkey, M., et al., "Expression of the regeneration-associated protein SPRR1A in primary sensory neurons and spinal cord of the adult mouse following peripheral and central injury", Journal of Comparative Neurology, 513(1):51-68, 2009.

* cited by examiner

*Primary Examiner* — Carla J Myers

(57) ABSTRACT

Described herein are methods used for the detection of gingivitis and the monitoring of gingivitis in a subject.

10 Claims, 8 Drawing Sheets

Specification includes a Sequence Listing.

25 exRNA biomarker candidates

| Number | Probe | log2(G) | log2(H) | log2FC | FC | absolute FC | P-value | Gene Accession | Gene Symbol | mRNA Source |
|---|---|---|---|---|---|---|---|---|---|---|
| 1 | TC01004752.hg.1 | 12,89742293 | 14,43722223 | -1,539799302 | -2,90754053 | 2,90754053 | 0,043998722 | S73288 | SPRR1A | NONCODE |
| 2 | TC10001257.hg.1 | 9,449203655 | 10,52453283 | -1,075329177 | -2,10720281 | 2,10720281 | 0,028595332 | NM_001137548 | FAM25C | NM_001137548 |
| 3 | TC19001572.hg.1 | 9,386668763 | 10,45155737 | -1,064888608 | -2,09200835 | 2,092008346 | 0,034305009 | NM_032488 | CNFN | RefSeq |
| 4 | TC01003260.hg.1 | 7,61813712 | 8,60196623 | -0,98382718 | -1,97770702 | 1,97770718 | 0,013299082 | NM_005621 | S100A12 | RefSeq |
| 5 | TC10002940.hg.1 | 10,04811623 | 10,99101507 | -0,94289846 | -1,92238706 | 1,92238706 | 0,023415694 | NM_001146157 | FAM25A | NM_001146157 |
| 6 | TC01004746.hg.1 | 6,832827463 | 7,745332919 | -0,912505456 | -1,88231158 | 1,88231577 | 0,02857103 | AJ243662 | CRCT1 | NONCODE |
| 7 | TC01001227.hg.1 | 6,650301215 | 7,497721041 | -0,847419827 | -1,79928014 | 1,799280142 | 0,045852944 | NM_019060 | CRCT1 | RefSeq |
| 8 | TC09000335.hg.1 | 7,64696791 | 8,405689683 | -0,758722293 | -1,69199147 | 1,691991467 | 0,027650545 | NM_000700 | ANXA1 | RefSeq |
| 9 | TC6_qbl_hap6000044.hg.1 | 6,730429749 | 7,467820783 | -0,737391033 | -1,66715823 | 1,667158226 | 0,034256888 | NM_001010909 | MUC21 | NM_001010909 |
| 10 | TC01003248.hg.1 | 6,762322031 | 7,454235802 | -0,691913771 | -1,615425 | 1,615425 | 0,001795997 | NM_178435 | LCE3E | RefSeq |
| 11 | TC6_mann_hap4000046.hg.1 | 6,805671575 | 7,493847589 | -0,688176014 | -1,61124515 | 1,611245148 | 0,028516286 | NM_001010909 | MUC21 | NM_001010909 |
| 12 | TC19002637.hg.1 | 5,681987008 | 6,321517483 | -0,639530475 | -1,55782208 | 1,557822084 | 0,012598595 | NM_001145641 | SRRM5 | RefSeq |
| 13 | TC05003317.hg.1 | 6,726280516 | 6,102666363 | 0,623361688 | 1,540460498 | 1,540460498 | 0,000123194 | — | — | NONCODE |
| 14 | TC02003331.hg.1 | 5,880871804 | 5,261569491 | 0,619302313 | 1,536132128 | 1,536132128 | 0,000277776 | OTTHUMT000032814 | AC073046.25 | NONCODE |
| 15 | TC20000876.hg.1 | 6,70889581 | 7,312806291 | -0,603910481 | -1,51983055 | 1,519830548 | 0,049563867 | NM_003064 | SLPI | RefSeq |
| 16 | TC12001536.hg.1 | 6,469755518 | 7,072607973 | -0,602852455 | -1,51871636 | 1,518716363 | 0,025723389 | NM_002272 | KRT4 | RefSeq |
| 17 | TC6_cox_hap2000051.hg.1 | 6,779052258 | 7,378021915 | -0,598969657 | -1,51463446 | 1,514634459 | 0,031355532 | NM_001010909 | MUC21 | NM_001010909 |
| 18 | TC14001693.hg.1 | 6,437339931 | 7,010928262 | -0,573588331 | -1,48822053 | 1,488220535 | 0,025002399 | NR_003225 | LGALS3 | soluble |
| 19 | TC17000416.hg.1 | 6,079404413 | 6,651778931 | -0,572375519 | -1,48696998 | 1,48696977 | 0,024712856 | NM_001001435 | CCL4L1 | RefSeq |
| 20 | TC09000621.hg.1 | 6,003365198 | 6,517492302 | -0,514127104 | -1,4281298 | 1,428129795 | 0,00028009 | NM_001005234 | OR1L3 | subfamily L |
| 21 | TC06002615.hg.1 | 5,824887582 | 5,318054756 | 0,506832826 | 1,420927382 | 1,420927382 | 0,019848073 | AJ420500 | SOX4 | NONCODE |
| 22 | TC02003412.hg.1 | 5,497792825 | 5,990392649 | -0,492599824 | -1,40697805 | 1,406978052 | 0,000894124 | — | — | NONCODE |
| 23 | TC01005710.hg.1 | 5,951820479 | 6,462290309 | -0,489530171 | -1,40398757 | 1,403987577 | 0,000676414 | OTTHUMT000003369 | RP5-965F6.2 | NONCODE |
| 24 | TC17001419.hg.1 | 5,932996225 | 6,419256935 | -0,486260709 | -1,40080944 | 1,400809438 | 0,000368636 | — | — | GenBank |
| 25 | TC19001957.hg.1 | 6,50932351 | 6,995393672 | -0,486070162 | -1,40062444 | 1,400624435 | 0,030337381 | BC127843 | PET100 | NONCODE |

Figure 1

|  |  | Association with disease | | | |
| --- | --- | --- | --- | --- | --- |
| Biomarker Name | Biomarker # | Microarray FC | | PCR slope | |
|  |  | direction | p-value | direction | p-value |
| NONHSAT006501.2 | m1 | - | 0.044 | - | <0.001 |
| NONHSAT071649 | m2 | + | <0.001 | + | <0.001 |
| NONHSAT005224 | m3 | + | <0.001 | + | <0.001 |
| NR_003225 | m4 | - | 0.025 | - | <0.001 |
| AF156166 | m5 | + | <0.001 | + | <0.001 |
| AJ420500 | m6 | + | <0.020 | + | <0.001 |
| NM_001146157 | m7 | - | 0.023 | - | 0.003 |
| AL832615 | m8 | - | <0.001 | NS* | 0.867 |
| NM_003064 | m9 | - | 0.049 | NS* | 0.088 |
| NM_019060 | m10 | - | 0.046 | - | <0.001 |

Values reported as direction of effect +/- and p-value for statistical significance

Figure 2

| Subject # | Gender | Age (years) | Index Score | SCRN | BASE | 3 WEEK | 6 WEEK |
|---|---|---|---|---|---|---|---|
| 1 | M | 28 | G | 1.9 | 1.29 | 1.24 | 0.90 |
| 2 | F | 29 | P | 1.59 | 2.66 | 2.61 | 1.90 |
| 3 | F | 28 | G | 1.84 | 1.61 | 1.79 | 0.81 |
| 4 | M | 29 | P | 2.4 | 1.85 | 1.69 | 1.09 |
| 5 | F | 41 | G | 1.19 | 1.79 | 1.64 | 0.82 |
| 6 | M | 26 | P | 1.52 | 1.72 | 1.79 | 1.21 |
| 7 | F | 24 | G | 1.35 | 1.7 | 1.85 | 0.81 |
| 8 | F | 33 | P | 2.79 | 2.35 | 2.01 | 2.00 |
| 9 | F | 53 | G | 1.58 | 1.85 | 1.94 | 0.70 |
| 10 | F | 23 | P | 2.05 | 2.1 | 1.84 | 1.38 |
| 11 | F | 20 | G | 1.64 | 1.83 | 1.87 | 1.84 |
| 12 | M | 21 | P | 2.16 | 2.22 | 2.18 | 2.13 |
| 13 | F | 20 | G | 1.6 | 1.67 | 1.96 | 0.86 |
| 14 | F | 21 | P | 2.87 | 2.14 | 2.21 | 1.73 |
| 15 | M | 35 | G | 1.8 | 2.11 | 2.1 | 1.77 |
| | | | P | 1.95 | 2.28 | 2.02 | 1.95 |
| | | | G | 1.62 | 1.8 | 2.01 | 1.60 |
| | | | P | 2.29 | 2.02 | 2.01 | 2.20 |
| | | | G | 1.86 | 1.84 | 2.56 | 1.84 |
| | | | P | 3.15 | 2.09 | 2.56 | 2.01 |
| | | | G | 1.55 | 1.98 | 1.53 | 0.84 |
| | | | P | 2.22 | 3.05 | 2.57 | 1.40 |
| | | | G | 1.79 | 2.1 | 1.4 | 0.92 |
| | | | P | 2.02 | 2.14 | 1.62 | 1.70 |
| | | | G | 1.95 | 1.71 | 1.38 | 1.46 |
| | | | P | 2.19 | 2.27 | 2.02 | 2.22 |
| | | | G | 1.98 | 1.89 | 1.44 | 0.95 |
| | | | P | 2.39 | 2.55 | 2.4 | 1.47 |
| | | | G | 1.89 | 1.83 | 1.26 | |
| | | | P | 1.81 | 2.07 | 1.57 | |

| Subject # | Gender | Age (years) | Index Score | SCRN | BASE | 3 WEEK | 6 WEEK |
|---|---|---|---|---|---|---|---|
| 16 | M | 31 | G | 1.65 | 1.86 | 1.42 | 2.10 |
| 17 | M | 19 | P | 2.19 | 2.1 | 1.96 | 1.98 |
| 18 | F | 25 | G | 1.97 | 1.92 | 1.57 | 2.19 |
| 19 | M | 24 | P | 2.87 | 2.49 | 2.47 | 1.93 |
| 20 | M | 29 | G | 1.67 | 1.78 | 1.78 | 1.18 |
| 21 | M | 36 | P | 2.13 | 2.03 | 1.91 | 1.67 |
| 22 | M | 24 | G | 1.8 | 1.97 | 2.06 | 2.05 |
| 23 | F | 22 | P | 2.35 | 2.13 | 2.07 | 2.08 |
| 24 | F | 41 | G | 1.96 | 1.86 | 1.45 | 2.17 |
| 25 | M | 34 | P | 2.81 | 2.8 | 2.45 | 2.46 |
| 26 | F | 23 | G | 2.02 | 1.87 | 2.02 | 2.06 |
| 27 | F | 24 | P | 2.04 | 2 | 1.6 | 1.93 |
| 28 | F | 23 | G | 2.1 | 1.8 | 1.77 | 0.91 |
| 29 | M | 21 | P | 2.61 | 2.3 | 1.8 | 1.46 |
| 30 | F | 39 | G | 2.14 | 2.41 | 1.49 | 0.99 |
| | | | P | 2 | 1.94 | 1.78 | 1.62 |
| | | | G | 2.92 | 2.81 | 2.42 | 1.96 |
| | | | P | 1.56 | 1.72 | 1.17 | 2.16 |
| | | | G | 1.94 | 2.2 | 1.64 | 0.86 |
| | | | P | 1.64 | 2.3 | 1.31 | 1.39 |
| | | | G | 3.39 | 2.3 | 1.64 | 1.97 |
| | | | P | 1.81 | 1.7 | 1.77 | 2.08 |
| | | | G | 2.18 | 2.13 | 1.85 | 2.01 |
| | | | P | 1.76 | 1.64 | 2.14 | 2.36 |
| | | | G | 2.28 | 2.85 | 1.8 | 1.92 |
| | | | P | 1.88 | 1.71 | 2.16 | 2.21 |
| | | | G | 2.26 | 3.07 | 1.62 | 2 |
| | | | P | 2 | 1.63 | 2.34 | 2.4 |
| | | | G | 1.79 | 2.11 | 1.96 | 2 |
| | | | P | | | 2.26 | 1.95 |

Figure 5

SALIVARY EXTRACELLULAR RNA BIOMARKERS FOR GINGIVITIS

CROSS-REFERENCE TO RELATED APPLICATIONS

This application claims the benefit of priority from U.S. Provisional Application No. 62/577,877, filed Oct. 27, 2017, the contents of which are hereby incorporated herein by reference in their entirety.

BACKGROUND

Periodontal diseases are the most common inflammatory disease affecting up to 90% of the population worldwide (Pihlstrom et al., 2005, Lancet, 366, 1809-20). Gingivitis, the reversible form of the disease, is induced by the accumulation of bacterial biofilm, and comprises the majority of the cases of patients with periodontal diseases (>75%) (Albandar et al., 1999, J Periodontol 70, 30-43; Tomar et al., 2000, J Periodontol., 71, 743-751). If left untreated, gingivitis may progress to periodontitis, which involves bone and attachment loss and it is mostly irreversible. Periodontitis can advance to the point that it induces tooth mobility and tooth loss. It may also adversely affect systemic health via ischemic stroke, cardiovascular events or cancers (Binder et al., 2015, Oncotarget 6, 22613-23; Mitsuhashi et al., 2015, Oncotarget, 6, 7209-7220). The common risk factors for periodontitis could be divided into inherited (e.g., genetic variants), and those that are acquired (e.g., socio-economic factors, poor oral hygiene, cigarette smoking and diabetes) (Chapple et al., 2017, Journal of Clinical Periodontology, 44 (Suppl 18), S39-S51).

The quest to develop salivary biomarkers for periodontal diseases has been elusive (Giannobile et al., 2009, Periodontol 2000, 50, 52-64). Despite the scientific acceptance of salivary biomarkers for the detection of gingivitis (Henskens et al., 2003, J Periodontal Res., 28, 43-48; Kinney et al., 2011, J. Dent. Res., 90, 752-8; Lee et al., 2012, J Periodontol., 83, 79-89; Shaila et al., 2013; J Indian Soc Periodontol., 17, 42-46; Morelli et al., 2014, J Periodontol., 85, 1770-8), the absence of definitively validated biomarkers prevents the regulatory approval and translation of a diagnostic test into clinical practice. Presently, the gold standard for early detection and diagnosis for gingivitis mainly includes a comprehensive periodontal exam along with subjective visual inspection (i.e. redness, swelling or gingival bleeding) performed during dental examinations. Bleeding upon probing, confirms the presence of gingivitis. Unfortunately, the absence of pain in gingivitis often renders individuals unaware of their pathologic gingival condition, particularly if they do not have to visit the dentist regularly. Thus, it is desirable to develop objective and scientifically credible biomarkers for early detection and monitoring of gingivitis as many of the gingivitis cases are left untreated (Albandar et al., 1999, J Periodontol 70, 30-43; Tomar et al., 2000, J Periodontol., 71, 743-751).

Thus, there is a need in the art for improved compositions and methods for detecting gingivitis. The present invention satisfies this unmet need.

BRIEF SUMMARY

In one aspect, the present invention provides a method of diagnosing gingivitis in a subject. The method comprises detecting the level of at least one biomarker in a saliva sample of the subject, wherein the at least one biomarker is selected from the group consisting of NONHSAT006501.2, NONHSAT071649, NONHSAT005224, LGALS3, AF156166, SOX4, FAM25A, AL832615, SLPI, and CRCT1; detecting that the level of the at least one biomarker in the saliva sample of the subject is differentially expressed as compared to the level of the at least one biomarker in a comparator control, and detecting gingivitis in the subject when the level of the at least one biomarker in the saliva sample of subject is differentially expressed when compared with the level of the biomarker in the comparator control. In one embodiment, the comparator control is the level of the at least one biomarker in the saliva sample of a subject or population not having gingivitis. In one embodiment, the method comprises the further step of treating the subject for gingivitis.

In one embodiment, the method comprises detecting that the level of at least one biomarker selected from the group consisting of NONHSAT071649, NONHSAT005224, AF156166, and SOX4 is increased as compared to the level of the at least one biomarker in the comparator control. In on embodiment, the method comprises detecting that the level of at least one biomarker selected from the group consisting of NONHSAT006501.2, LGALS3, FAM25A, and CRCT1 is decreased as compared to the level of the at least one biomarker in the comparator control.

In one embodiment, the level of the at least one biomarker in the saliva sample is determined by measuring the level of mRNA of the at least one biomarker in the saliva sample. In one embodiment, the level of the at least one biomarker in the saliva sample is determined by measuring the level of polypeptide of the at least one biomarker in the saliva sample.

In one embodiment, the comparator control is at least one selected from the group consisting of a positive control, a negative control, a historical control, a historical norm, or the level of a reference molecule in the biological sample. In one embodiment, the subject is human.

In one aspect, the present invention provides a method of monitoring the response to a gingivitis treatment in a subject. The method comprises detecting the level of at least one biomarker in a saliva sample of the subject obtained after the treatment is initiated, wherein the at least one biomarker is selected from the group consisting of NONHSAT006501.2, NONHSAT071649, NONHSAT005224, LGALS3, AF156166, SOX4, FAM25A, AL832615, SLPI, and CRCT1; detecting that the level of the at least one biomarker in the saliva sample of the subject is differentially expressed as compared to the level of the at least one biomarker in a comparator control, and detecting that the subject is responsive to the treatment when the level of the at least one biomarker in the saliva sample of subject is differentially expressed when compared with the level of the biomarker of the comparator control. In one embodiment, the comparator control a saliva sample of the subject obtained prior to initiation of the treatment. In one embodiment, the comparator control comprises a saliva sample of the subject obtained at an earlier time point during the treatment.

In one aspect, the present invention provides a method comprising obtaining a saliva sample of a subject; and detecting the level of at least one biomarker in a saliva sample of the subject, wherein the at least one biomarker is selected from the group consisting of NONHSAT006501.2, NONHSAT071649, NONHSAT005224, LGALS3, AF156166, SOX4, FAM25A, AL832615, SLPI, and CRCT1. In one embodiment, the level of the at least one biomarker in the saliva sample is determined by measuring the level of mRNA of the at least one biomarker in the saliva sample. In one embodiment, the level of the at least one biomarker in the saliva sample is determined by measuring the level of polypeptide of the at least one biomarker in the saliva sample.

In one aspect, the present invention provides a method of treating gingivitis, comprising administering a gingivitis treatment to a subject identified as having a differential level of at least one biomarker selected from the group consisting of NONHSAT006501.2, NONHSAT071649, NONHSAT005224, LGALS3, AF156166, SOX4, FAM25A, AL832615, SLPI, and CRCT1 in a saliva sample of the subject.

In one aspect, the present invention provides a kit for detecting of gingivitis comprising a reagent that detects the presence of at least one biomarker selected from the group consisting of NONHSAT006501.2, NONHSAT071649, NONHSAT005224, LGALS3, AF156166, SOX4, FAM25A, AL832615, SLPI, and CRCT1 in a saliva sample.

In one aspect, the present invention provides a method of treating gingivitis in a subject, comprising detecting the level of at least one biomarker in a saliva sample of the subject, wherein the at least one biomarker is selected from the group consisting of NONHSAT006501.2, NONHSAT071649, NONHSAT005224, LGALS3, AF156166, SOX4, FAM25A, AL832615, SLPI, and CRCT1; detecting that the level of the at least one biomarker in the saliva sample of the subject is differentially expressed as compared to the level of the at least one biomarker in a comparator control, detecting gingivitis in the subject when the level of the at least one biomarker in the saliva sample of subject is differentially expressed when compared with the level of the biomarker in the comparator control; and administering a gingivitis treatment to the subject.

BRIEF DESCRIPTION OF THE DRAWINGS

The following detailed description of embodiments of the invention will be better understood when read in conjunction with the appended drawings. It should be understood that the invention is not limited to the precise arrangements and instrumentalities of the embodiments shown in the drawings.

FIG. 1 depicts the results of example experiments depicting the top 25 salivary exRNA biomarker candidates (Affymetrix HTA 2.0 microarray analysis).

FIG. 2 depicts the results of example experiments depicting the concordance of 10 salivary exRNA biomarker changes with initial microarray data.

FIG. 5 depicts a summary of demographic and clinical data for the subjects included in the validation phase.

DETAILED DESCRIPTION

Figure 3:
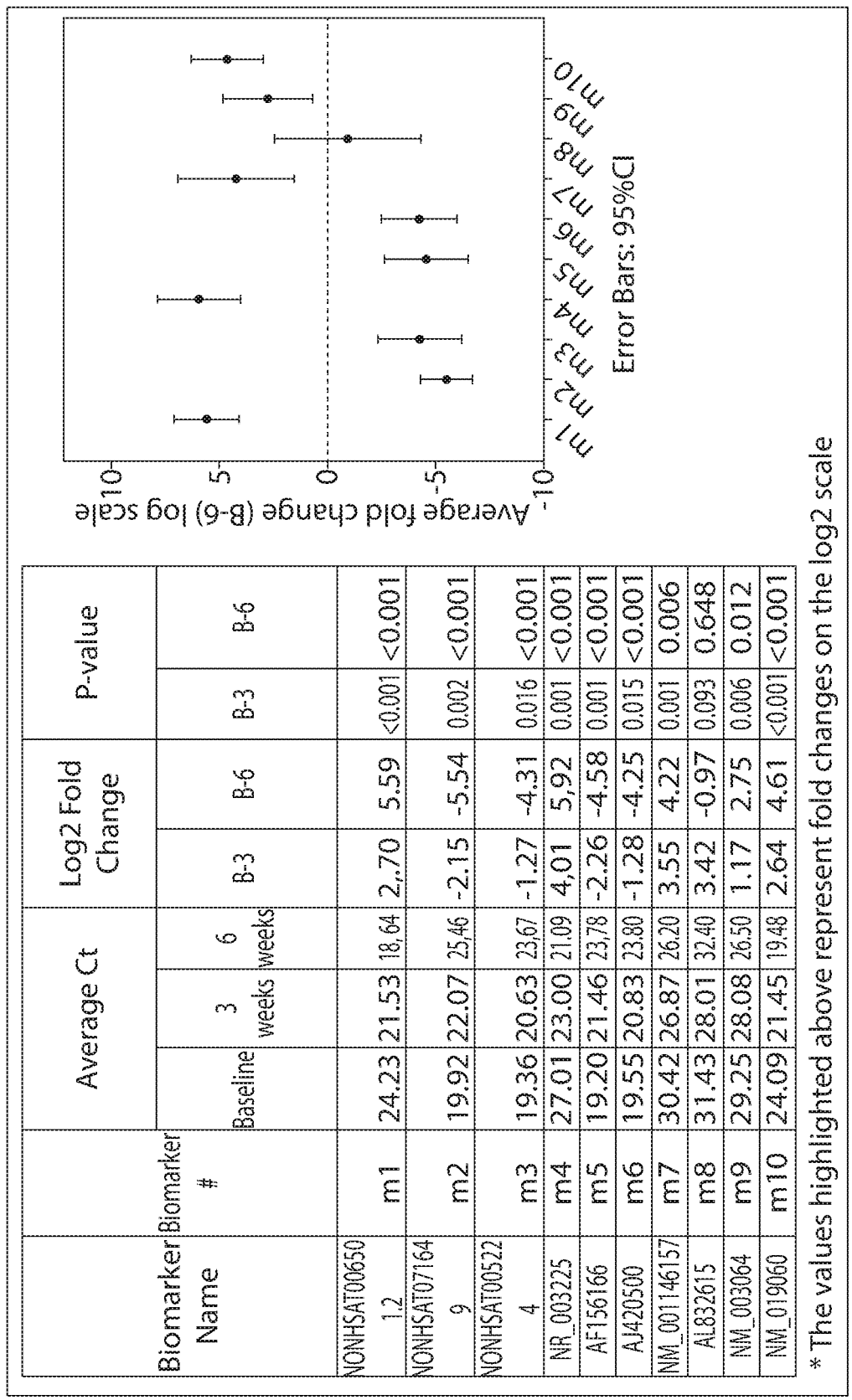
FIG. 3 depicts the results of example experiments depicting the validation of HTA 2.0 Affymetrix array profiling results by qRT-PCR. The list of 10 exRNAs with fold changes and p-values. A plot presenting the fold changes and 95% confidence interval (CI) for each of 10 salivary exRNA biomarkers on the log base 2 scale for the baseline-week 6 period.

The present invention provides methods to detect and measure saliva-based biomarkers for the detection of gingivitis in a subject. For example, in some embodiments, the biomarkers described herein can be used to assess the status of gingivitis, monitor gingivitis regression or monitor a response to gingivitis treatment. The markers of the invention can be used to screen, assess risk, diagnose and monitor gingivitis. The detection or diagnosis of gingivitis in a subject using the markers of the invention can be used to establish and evaluate treatment plans for gingivitis.

The present invention therefore provides compositions and methods of diagnosing and providing a prognosis for gingivitis, by examining relevant biomarkers and their expression. In one embodiment, biomarker expression includes transcription into messenger RNA (mRNA) and translation into protein, as well as transcription into types of RNA such as long non-coding RNA (lncRNA), transfer RNA (tRNA) and ribosomal RNA (rRNA) that are not translated into protein.

In one embodiment, the biomarkers for the detection of gingivitis or for monitoring of gingivitis regression or response to treatment includes but are not limited to the biomarkers provided in FIG. 1 or FIG. 2, including but not limited to SPRR1A, FAM25C, CNFN, S100A12, FAM25A, CRCT1, ANXA1, MUC21, LCE3E, SRRM5, AC073046.25, SLPI, KRT4, LGALS3, CCL4L1, OR1L3, SOX4, RP5-965F6.2, PET100, NONHSAT006501.2, NONHSAT071649, NONHSAT005224, AF156166, and AL832615.

In one embodiment, the biomarkers includes one or more lncRNAs selected from the group consisting of NONHSAT006501.2, NONHSAT071649, and NONHSAT005224. In one embodiment, the biomarkers includes one or more mRNAs selected from the group consisting of LGALS3, AF156166, SOX4, FAM25A, AL832615, SLPI, and CRCT1.

In some embodiments, the biomarkers described herein are extracellular biomarkers. For example, in some embodiments, the biomarkers described herein are extracellular biomarkers detected in saliva supernatant.

In some embodiments, the biomarkers are used in conjunction with one or more subject characteristics to detect or diagnose gingivitis. For example, the subject characteristics include, but is not limited to, gender, age, ethnicity, height, weight, diet, genetics, smoking, mouth-breathing, mouth-breathing during sleep, obesity, heart disease, osteoporosis, hypertension, diabetes, bowel diseases, muscle and joint disease, tumor, mental illness, caries, missing teeth, level of oral hygiene, level of dental care utilization, and use of medications that dry the mouth.

In some embodiments, the biomarkers are used in conjunction with one or more assays for gingivitis, including, but not limited to Löe-Silness Gingival Index (GI), Quigley and Hein Plaque Index (PI), Turesky-modification of the Quigly and Hein index, gingival bleeding index, Navy index, modified Navy index, bleeding on probing (BOP), and probing depth (PD).

Accordingly, in some embodiments of the invention, methods for diagnosing gingivitis is provided. The methods comprise a) providing a saliva sample from the subject; b) analyzing the saliva sample with an assay that specifically detects at least one biomarker of the invention in the saliva sample; c) comparing the subject biomarker profile with a control biomarker profile wherein a statistically significant difference between the subject biomarker profile and the control biomarker profile is indicative of gingivitis. In some embodiments, the methods further comprise the step of d) effectuating a treatment regimen based thereon.

In one embodiment, the biomarker types comprise RNA biomarkers. In various embodiments, the RNA is detected by at least one of mass spectroscopy, PCR microarray, thermal sequencing, capillary array sequencing, solid phase sequencing, and the like.

In another embodiment, the biomarker types comprise polypeptide biomarkers. In various embodiments, the polypeptide is detected by at least one of ELISA, Western blot, flow cytometry, immunofluorescence, immunohistochemistry, mass spectroscopy, and the like.

Definitions

Unless defined otherwise, all technical and scientific terms used herein have the same meaning as commonly understood by one of ordinary skill in the art to which this invention belongs. Any methods and materials similar or equivalent to those described herein can be used in the practice or testing of the present invention.

As used herein, the words "preferred" and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

Unless stated otherwise, all percentages of composition components given in this specification are by weight based on a total composition or formulation weight of 100%.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

As used herein the terms "alteration," "defect," "variation," or "mutation," refers to a mutation in a gene in a cell that affects the function, activity, expression (transcription or translation) or conformation of the polypeptide that it encodes. Mutations encompassed by the present invention can be any mutation of a gene in a cell that results in the enhancement or disruption of the function, activity, expression or conformation of the encoded polypeptide, including the complete absence of expression of the encoded protein and can include, for example, missense and nonsense mutations, insertions, deletions, frameshifts and premature terminations. Without being so limited, mutations encompassed by the present invention may alter splicing the mRNA (splice site mutation) or cause a shift in the reading frame (frameshift).

The term "amplification" refers to the operation by which the number of copies of a target nucleotide sequence present in a sample is multiplied.

By the term "applicator," as the term is used herein, is meant any device including, but not limited to, a hypodermic syringe, a pipette, an iontophoresis device, a patch, and the like, for administering the compositions of the invention to a subject.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. κ and λ light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

As used herein, the term "marker" or "biomarker" is meant to include a parameter (e.g., RNA, polypeptide, etc.) which is useful according to this invention for determining the presence and/or severity and/or stage of gingivitis.

The level of a marker or biomarker "significantly" differs from the level of the marker or biomarker in a reference sample or comparator if the level of the marker in a sample from the patient differs from the level in a reference sample or comparator by an amount greater than the standard error of the assay employed to assess the marker, for example at least 10%, 25%, 50%, 75%, or 100%.

The term "control or reference standard or comparator" describes a material comprising none, or a normal, low, or high level of one of more of the marker (or biomarker) expression products of one or more the markers (or biomarkers) of the invention, such that the control or reference standard or comparator may serve as a comparator against which a sample can be compared.

By the phrase "determining the level of marker (or biomarker) expression" is meant an assessment of the degree of expression of a marker in a sample at the nucleic acid or protein level, using technology available to the skilled artisan to detect a sufficient portion of any marker expression product.

"Differentially increased expression" or "up regulation" refers to biomarker product levels which are increased by at least 10% or more, for example, 20%, 30%, 40%, or 50%, 60%, 70%, 80%, 90% or more, and/or 1.1 fold, 1.2 fold, 1.4 fold, 1.6 fold, 1.8 fold, 2.0 fold or more, and any and all whole or partial increments therebetween than a control.

"Differentially decreased expression" or "down regulation" refers to biomarker product levels which are reduced or decreased by at least 10% or more, for example, 20%, 30%, 40%, or 50%, 60%, 70%, 80%, 90% or more, and/or 2.0 fold, 1.8 fold, 1.6 fold, 1.4 fold, 1.2 fold, 1.1 fold or more, and any and all whole or partial increments therebetween than a control.

A "disease" is a state of health of an animal wherein the subject cannot maintain homeostasis, and wherein if the disease is not ameliorated then the subject's health continues to deteriorate.

As used herein, an "immunoassay" refers to a biochemical test that measures the presence or concentration of a substance in a sample, such as a biological sample, using the reaction of an antibody to its cognate antigen, for example the specific binding of an antibody to a protein. Both the presence of the antigen or the amount of the antigen present can be measured.

As used herein, an "instructional material" includes a publication, a recording, a diagram, or any other medium of expression which can be used to communicate the usefulness of a component of the invention in a kit for detecting biomarkers disclosed herein. The instructional material of the kit of the invention can, for example, be affixed to a container which contains the component of the invention or be shipped together with a container which contains the component. Alternatively, the instructional material can be shipped separately from the container with the intention that the instructional material and the component be used cooperatively by the recipient.

The term "label" when used herein refers to a detectable compound or composition that is conjugated directly or indirectly to a probe to generate a "labeled" probe. The label may be detectable by itself (e.g., radioisotope labels or fluorescent labels) or, in the case of an enzymatic label, may catalyze chemical alteration of a substrate compound or composition that is detectable (e.g., avidin-biotin). In some instances, primers can be labeled to detect a PCR product.

The "level" of one or more biomarkers means the absolute amount or relative amount or concentration of the biomarker in the sample.

The term "marker (or biomarker) expression" as used herein, encompasses the transcription, translation, post-translation modification, and phenotypic manifestation of a gene, including all aspects of the transformation of information encoded in a gene into RNA or protein. By way of non-limiting example, marker expression includes transcription into messenger RNA (mRNA) and translation into protein, as well as transcription into types of RNA such as transfer RNA (tRNA) and ribosomal RNA (rRNA) that are not translated into protein.

The terms "microarray" and "array" refers broadly to both "DNA microarrays" and "DNA chip(s)," and encompasses all art-recognized solid supports, and all art-recognized methods for affixing nucleic acid molecules thereto or for synthesis of nucleic acids thereon. In some instances, arrays comprise a plurality of different nucleic acid probes that are coupled to a surface of a substrate in different, known locations. These arrays, also described as "microarrays" or colloquially "chips" have been generally described in the art, for example, U.S. Pat. Nos. 5,143,854, 5,445,934, 5,744,305, 5,677,195, 5,800,992, 6,040,193, 5,424,186 and Fodor et al., 1991, Science, 251:767-777, each of which is incorporated by reference in its entirety for all purposes. Arrays may generally be produced using a variety of techniques, such as mechanical synthesis methods or light directed synthesis methods that incorporate a combination of photolithographic methods and solid phase synthesis methods. Techniques for the synthesis of these arrays using mechanical synthesis methods are described in, e.g., U.S. Pat. Nos. 5,384,261, and 6,040,193, which are incorporated herein by reference in their entirety for all purposes. In one embodiment, the array is a planar array surface. In some embodiments, the array is fabricated on a surface of virtually any shape or even a multiplicity of surfaces. Arrays may be nucleic acids on beads, gels, polymeric surfaces, fibers such as fiber optics, glass or any other appropriate substrate. (See U.S. Pat. Nos. 5,770,358, 5,789,162, 5,708,153, 6,040,193 and 5,800,992, which are hereby incorporated by reference in their entirety for all purposes.) Arrays may be packaged in such a manner as to allow for diagnostic use or can be an all-inclusive device; e.g., U.S. Pat. Nos. 5,856,174 and 5,922,591 incorporated in their entirety by reference for all purposes. Arrays are commercially available from, for example, Affymetrix (Santa Clara, Calif.) and Applied Biosystems (Foster City, Calif.), and are directed to a variety of purposes, including genotyping, diagnostics, mutation analysis, marker expression, and gene expression monitoring for a variety of eukaryotic and prokaryotic organisms. The number of probes on a solid support may be varied by changing the size of the individual features. In one embodiment the feature size is 20 by 25 microns square, in other embodiments features may be, for example, 8 by 8, 5 by 5 or 3 by 3 microns square, resulting in about 2,600,000, 6,600,000 or 18,000,000 individual probe features.

"Measuring" or "measurement," or alternatively "detecting" or "detection," means assessing the presence, absence, quantity or amount (which can be an effective amount) of either a given substance within a clinical or subject-derived sample, including the derivation of qualitative or quantitative concentration levels of such substances, or otherwise evaluating the values or categorization of a subject's clinical parameters.

By the term "modulating," as used herein, is meant mediating a detectable increase or decrease in the activity and/or level of a mRNA, polypeptide, or a response in a subject compared with the activity and/or level of a mRNA, polypeptide or a response in the subject in the absence of a treatment or compound, and/or compared with the activity and/or level of a mRNA, polypeptide, or a response in an otherwise identical but untreated subject.

A "normal" subject does not have a clinical manfestation of gingivitis. In some instances a "normal" subject has a depth of gingival pocket of less than about 3 mm.

The terms "patient," "subject," "individual," and the like are used interchangeably herein, and refer to any animal, or cells thereof whether in vitro or in situ, amenable to the methods described herein. In some non-limiting embodiments, the patient, subject or individual is a human.

As used herein, the term "providing a prognosis" refers to providing a prediction of the probable course and outcome of diabetes, including prediction of severity, duration, chances of recovery, etc. The methods can also be used to devise a suitable therapeutic plan, e.g., by indicating whether or not the condition is still at an early stage or if the condition has advanced to a stage where aggressive therapy would be ineffective.

A "reference level" of a biomarker means a level of the biomarker that is indicative of a particular disease state, phenotype, or lack thereof, as well as combinations of disease states, phenotypes, or lack thereof. A "positive" reference level of a biomarker means a level that is indicative of a particular disease state or phenotype. A "negative" reference level of a biomarker means a level that is indicative of a lack of a particular disease state or phenotype.

The term "risk stratification," according to the invention, comprises finding patients for the purpose of diagnosis and therapy/treatment (of sequelae) of gingivitis, with the goal of allowing as advantageous a course of the gingivitis as possible.

"Sample" or "biological sample" as used herein means a biological material isolated from an individual. The biological sample may contain any biological material suitable for detecting the desired biomarkers, and may comprise cellular and/or non-cellular material obtained from the individual. One example of a biological sample is a whole saliva sample. Another example of a biological sample is a cell-free saliva sample. Another example of a biological sample is a saliva supernatant, such as the supernatant obtained after centrifuging a saliva sample. Another example of a biological sample is the material in a pellet obtained from a saliva sample, such as a pellet obtained after centrifuging a saliva sample (i.e., saliva pellet).

"Standard control value" as used herein refers to a predetermined amount of a particular protein or nucleic acid that is detectable in a saliva sample, either in whole saliva or in a saliva pellet or in a saliva supernatant. The standard control value is suitable for the use of a method of the present invention, in order for comparing the amount of a protein or nucleic acid of interest (e.g., marker, biomarker) that is present in a saliva sample. An established sample serving as a standard control provides an typical amount of the protein or nucleic acid of interest in the saliva that is typical for an typical, healthy person of reasonably matched background, e.g., gender, age, ethnicity, and medical history. A standard control value may vary depending on the protein or nucleic acid of interest and the nature of the sample (e.g., whole saliva, saliva supernatant, etc.).

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention is based on the identification of extracellular biomarkers present in or absent from a saliva supernatant sample that can identify a subject as having gingivitis, monitor gingivitis regression in a subject, and monitor a response to gingivitis treatment in a subject.

In one embodiment, the invention provides a biomarker for the detection of gingivitis. In one embodiment, the biomarkers includes one or more lncRNAs selected from the group consisting of NONHSAT006501.2, NONHSAT071649, and NONHSAT005224. In one embodiment, the biomarkers includes one or more mRNAs selected from the group consisting of LGALS3, AF156166, SOX4, FAM25A, AL832615, SLPI, and CRCT1.

In one embodiment, the invention provides a method of detecting or diagnosing gingivitis in a subject, comprising measuring the level of at least one of NONHSAT006501.2, NONHSAT071649, NONHSAT005224, LGALS3, AF156166, SOX4, FAM25A, AL832615, SLPI, and CRCT1 in a saliva sample of a subject. In one embodiment, the invention provides a method of detecting or diagnosing gingivitis in a subject, comprising measuring the level of NONHSAT006501.2; NONHSAT071649; FAM25A; and CRCT1 in a saliva sample of a subject.

In one embodiment, the invention provides a method monitoring gingivitis regression or response to gingivitis treatment in a subject, comprising measuring the level of at least one of NONHSAT006501.2, NONHSAT071649, NONHSAT005224, LGALS3, AF156166, SOX4, FAM25A, AL832615, SLPI, and CRCT1 in a saliva sample of a subject.

Biomarkers

The present invention provides a biomarker for the detection of gingivitis. In one embodiment, the biomarkers includes one or more lncRNAs selected from the group consisting of NONHSAT006501.2, NONHSAT071649, and NONHSAT005224. In one embodiment, the biomarkers includes one or more mRNAs selected from the group consisting of LGALS3, AF156166, SOX4, FAM25A, AL832615, SLPI, and CRCT1.

In one embodiment, the biomarker comprises NONHSAT006501.2. In some embodiments NONHSAT006501.2 may also be referred to as having a GenBank Accession No. of 573288, or as having a gene symbol of SPRR1A, or as having a Noncode Gene ID of NONHSAG002962.2, or as having a lncipedia ID of lnc-SPRR1A-1-1_dup1,lnc-S. In one embodiment NONHSAT006501.2 comprises a nucleotide sequence of: GTAATGTGGTCCACAGCCATGCCCTTGAGGAGCTGGCCACTGGATACTGAACACCCTACTCCATTCTGCTTATGAATCCCATTTGCCTATTGACCCTGCAGTTAGC ATGCTGTCACCCTGAATCATAATCGCTCCTTTGCACCTCTAAAAAGATGTCCCTTACCCTCATTCTGGAGGGCTCCTGAGCCTCTGCGTAAGGCTGAACGTCTCAC TGACTGAGCTAGTCTTCTTGTTGCTCGGGTGCATTTGAGGATGGATTTGGGGAAGGATCAAGTGAACCATCCCTAGTCTTCCTTCAATAAATAACTTTTAACTCC (SEQ ID NO: 1). However, NONHSAT006501.2 is not limited to the sequence of SEQ ID NO: 1, but rather encompasses other isoforms or variants.

In one embodiment, the biomarker comprises NONHSAT071649. In some embodiments NONHSAT071649 may also be referred to as OTTHUMT00000328143, or as having a gene symbol of AC073046.25, or as having a lncipedia ID of lnc-TET3-2-1_dup1. In one embodiment NONHSAT071649 comprises a nucleotide sequence of: CGCTCCGCCCCGGAGGCGGCGGGCAGGCAGCACTGCCTTCTCCAGCGTCCAG ACCCTGGAGGAAAAATACCAGGAGAAACTGCTCACTCAGCTCTGCCCCCACCACACCCCTACCTGCTCAACTCATGCCTGGGTCCAGGGTGGGTGAGGGTGAAGAACCCACCGGGCCAAGATGATCCCTTTTCTGAGGGCTGCTGCTGGTGTCCTCC CCCAGATCCTGGGCCCCAGCAGGTGGGAGAGTGGCCCCCTACGGAGTCCGATCAGACTGCTGCAGAGGAGGTGAAGAGGGGTTGAGAAGAGGCATCCATCCAC GAGACTGAAGCCACTTGCCTTCACCCTTGTAGACTCTTGACTGTTCTAGGCGAGAAGGACCTGTTGGTGGCCTTTGGA (SEQ ID NO: 2). However, NONHSAT071649 is not limited to the sequence of SEQ ID NO: 2, but rather encompasses other isoforms or variants.

In one embodiment, the biomarker comprises NONHSAT005224. In some embodiments NONHSAT005224 may also be referred to as OTTHUMT00000033693, or as having a gene symbol of RP5-965F6.2, or as having a lncipedia ID of lnc-ST7L-2-1_dup1. In one embodiment NONHSAT005224 comprises a nucleotide sequence of: TTTCTCAGCCTGGAGACTGAAAGCTCTCTTTGGCTGTTGGCCCTCCCAGGCAGAGTCCACTGGCTGTTAGGGTGAAATGGGGCTGATGCTTCCTGGAATCCACCA GAAGTATGCAAATTGCACCATCTCTTTCAGCTGCCTGCGCCTGCATTCCATCG AGGATTCCGGCTCGTCCCCCAGTGGCAACAACTAGAGAGGAGGTGAGGATCC CCGGCGCTGCCATCTGATAGGCTGTCTCCCTAGCTCCTCTTGCACTGGCAATC CTTTCATCACACAGGCCTTGTTTTGAAGGGACCTATTCCACCCACAGTCGTTT CTCACCTCTAGGAGGCCAAAAAGCTGTAGTCATTGCTGTGGTATCAGGAACT CGAGTTCCTCTCAGAGGTGTTGTGAAGAGCTTCCCTTCCAACAGTACATGGCC TAAATACCAGGGAGGAAGTTTCTGACTTTTTCCATCTTCAGTAAAACAGAACC TCTGTTGTGGATGCAGTGGCTTTGCAAGGAGAGTGGCATTGTCTCTTGGTGAA TGTAGTTGTTCAAGTCATGG (SEQ ID NO: 3). However, NONHSAT005224 is not limited to the sequence of SEQ ID NO: 3, but rather encompasses other isoforms or variants.

In one embodiment, the biomarker comprises LGALS3. In some embodiments LGALS3 may also be referred to as having a GenBank Accession No. of NR 003225. In one embodiment LGALS3 comprises a nucleotide sequence of: GTGTGCAAATAGAGGAATAAATAGCAGGGCAGCAACTATGTCTGGAGGTCAT TGTCTTTCCTGTCTCAGTAGTAATCAATCACTGCTTATCTTCAAAAACCCAGA GTAGGGGATGGGGCAGTTAGTGGGGACAGAGGGCAGATGGGTAAGATTCAG AGCACAGGCTAGTGTGACGGAAGTTTAAACTTGTGAGTTAAATAGGGTTTGG CAATCTAGCTGGATAGCATCCCTGCCCCTTGAAGAGATGTTTTTGTGGCGCCA CACTACTGACTTAGGCATAATGCCTAGAGATGGATTAGAACTGCACAATGAA CTAGTGGTGAGGTTCAGTTTAATGGAAATTGGTGAAAGCTTTTAGGATAAAA TGATAATCTTTGTTTCTTTCAGGAAAATGGCAGACAATTTTTCGGTAAGTGTT TTATGCCTGTTTCTTCCCCTTGATCAGCTCCACATGGTTGAGGGTTGGGGGTTT TGTTTTTACCATGACTTTCCCTTTTCACTCTCCCACTGCGTGGCTTCCCCTGGA CTCATTTGTCCAATGAGGGCTTGCAAGCTGGAGCCTTGTTTTCCAGCAGCAG ATTTGGGAAGAAAGCCAGGCAGAGCGAGGCCTGGGACTCACTCACAGTAAC CCTTTCACCAAAAGGCCCAGGGCGGAAGGGAGTGGACTCTGCCGGCAGGAG CTGAGAAATCCTCTGAGTAGCGGGAAGTGCGGTACAGTCTGGGCATTCTGAT GTTTGTGATTGTTTTTCTCACGGTGATGAAAAAGTATGTGCTATAAGTAGAGG AGCGCTAACTCCTGACTTGAGCTAATTATGAAAATGCAGCCCTCCCTGATCTG AGACGTTGGGAGGCAAGAATAAAGTGAAAAAGTATATGTAATCCAACATCT AATTTTAGTCTTAGAAACTCAAACTATTAATAAGTGGAAAAAGTTTAATGAT ATGCATGTAATGCCTTTGCCATATTCCTCTCCTTCTTAGATCACATATTCCTAT TTTCCTGAAAATTCTGCTTTTGAGAATGCTTTCTGTCCCGTAATTGTGTATGTC TTTCTTTCCAGCTCCATGATGCGTTATCTGGGTCTGGAAACCCAAACCCTCAA GGATGGCCTGGCGCATGGGGGAACCAGCCTGCTGGGGCAGGGGCTACCCA GGGGCTTCCTATCCTGGGGCCTACCCCGGGCAGGCACCCCCAGGGGCTTATC CTGGACAGGCACCTCCAGGCGCCTACCCTGGAGCACCTGGAGCTTATCCCGG AGCACCTGCACCTGGAGTCTACCCAGGCCACCCAGCGGCCCTGGGGCCTAC CCATCTTCTGGACAGCCAAGTGCCACCGGAGCCTACCCTGCCACTGGCCCCT ATGGCGCCCCTGCTGGCCCACTGATTGTGCCTTATAACCTGCCTTTGCCTGGG GGAGTGGTGCCTCGCATGCTGATAACAATTCTGGGCACGGTGAAGCCCAATG CAAACAGAATTGCTTTAGATTTCCAAAGAGGGAAT-GATGTTGCCTTCCACTTT AACCCACGCTTCAAT-GAGAACAACAGGAGAGTCATTGTTTGCAATA-CAAAGC TGGATAATAACTGGGGAAGGGAAGAAA-GACAGTCGGTTTTCCCATTTGAAAG TGGGAAAC-CATTCAAAATACAAGTACTGGTTGAACCTGAC-CACTTCAAGGTT GCAGTGAATGATGCTCACTTGTTGCAGTACAAT-CATCGGGTTAAAAAACTCA ATGAAATCAGCAAACTGGGAATTTCTGGTGACATA-GACCTCACCAGTGCTTC ATATACCATGATATAATCT-GAAAGGGGCAGATTAAAAAAAAAAAAAGAATC TAAACCTTACATGTGTAAAGGTTTCATGTTCACTGT-GAGTGAAAATTTTTACA TTCAT-CAATATCCTCTTGTAAGTCATCTACTTAATAAATAT-TACAGTGAATT ACCTGTCTCAATATGT-CAAAAAAAAAAAAAAAAAAA (SEQ ID NO: 4). However, LGALS3 is not limited to the sequence of SEQ ID NO: 4, but rather encompasses other isoforms or variants.

In one embodiment, the biomarker comprises AF156166. In some embodiments AF156166 may also be referred to as having a GenBank Accession No. of AF156166 in one embodiment AF156166 comprises a nucleotide sequence of:

(SEQ ID NO: 5)
GAGACTGCATAGGGCTCGGCGTGGATCTTGTTAATGCTGATTCTGGTACA

GTAGGTCTAGGGCGGGGCCTGAGATTCTGCATTTCTAACAAGAACCCAGG

TGATGCTGACGCTGCTGGGCCAAAAAAGACACTTTGAGTAGCAAGGGTTA

GGCAACCTTTAAAGGGCCCTTCAAGAGTCTAAGATTCCATGAAGGATACT

ATTTCCTCTACAAGCTTGTGAAAGTCTTCCAGTGCTACTGGGAATGGGGT

ACAGGGATAAATCTCACTGTTTTGACCTCACAGAAGTAAACCCCTAGAAT

CATGTTCTCAAAATGAAACACTGGATTGCTGAACTGATGGCATTGAGAAT

TAAGGCTCCAAAATCCTGGGAGTTTCATACCTAACTCCACTGCCTTTGCC

TTATGATGCACACTGCTCCCTCTATCCCTCCCTCCCAGGGTCTGCAGAGA

TGAACTATGCTGTTTTAGGTCTCATTGGTCCTTATACCTTCCCTAAACCA

GGAGGACTTTGGAGCCTGCTGACACAGGGAGTTCTACATGTCTAAGCACG

CAGCTGCTAGAGTCCTCAGCCATCTGAGCTAAATAGCTGCTCAGAGACAA

TTAGTACACCTCCGTATYTTACAGATAAAGGAACTGAAGTCCAAACAAGC

CAAGCTACCCAACCAAGGCTCACAGCAGGCAAGAGGATAAAAACCATGTC

CTTTGACTCCCAGGTTAGTTTT.

However, AF156166 is not limited to the sequence of SEQ ID NO: 5, but rather encompasses other isoforms or variants.

In one embodiment, the biomarker comprises SOX4. In some embodiments SOX4 may also be referred to as having a GenBank Accession No. of AJ420500. In one embodiment SOX4 comprises a nucleotide sequence of: CCACGCGTCCGCATAT-TTTTTCTTTTGTCCCTTTTTTTCTTTCCTTTCTTTT-TACT TCCTTTATTTCTTTAT-TCCTTCCTTTTCCTTTTTTTCTTTTTTTTTTCTTTTT-TTTT TTTTTTGGTAGTTGTTGTTACCCACGCCAT-TTTACGTCTCCTTCACTGAAGGG CTAGAGTTT-TAACTTTTAATTTTTTATATTTAAATGTA-GACTTTTGACACTTTT AAAAAACAAAAAAAGACAAGAGAGAT-GAAAACGTTTGATTATTTTCTCAGTG TAT-TTTTGTAAAAAATATATAAAGGGGGTGT-TAATCGGTGTAAATCGCTGTTT GGATTTCCTGATTTTATAACAGGGCGGCTGGT-TAATATCTCACACAGTTTAAAAAATCAGCCCCTAAT-TTCTCCATGTTTACACTTCAATCTGCAGGCTTCT-TAAA GTGACAGTATCCCTTAACCTGCCACCAGTGTC-CACCCTCCGGCCCCGTCTTG TAAAAAGGGGAG-GAGAATTAGCCAAACACTGTAAGCTTT-TAAGAAAAACAA AGTTTTAAACGAAATACTGCTCTGTCCAGAGGCTT-TAAAACTGGTGCAATTAC AGCAAAAAGGGAT-TCTGTAGCTTTAACTTGTAAACCA-CATCTTTTTGCACTT TTTTTATAAGCAAAAACGTGCCGTTTAAACCACTG-GATCTATCTAAATGCCGA TTTGAGTTCGCGACAC-TATGTACTGCGTTTTTCATTCTTGTATTTGACTATTTA ATCCTTTCTACTTGTCGCTAAATATAATTGTTT-TAGTCTTATGGCATGATGATA GCATATGTGTTCAGGTTTATAGCTGTTGTGTT-TAAAAATTGAAAAAAGTGGAA AACATCTTTGTA-CATTTAAGTCTGTATTATAATAAGCAAAAAGAT-TGTGTGTA TGTATGTTTAATATAA-CATGACAGGCACTAGGACGTCTGCCTTTT-TAAGGCAG TTCCGTTAAGGGTTTTTGTTTT-TAAACTTTTTTTTGCCATCCATCCTGTGCAAT ATGCCGTGTAGAATATTTGTCTTAAAATTCAAGGC-CACAAAAACAATGTTTG GGG-GAAAAAAAAGAAAAAATCATGCCAGCTAAT-CATGTCAAGTTCACTGCCT GTCAGATTGTTGA-TATATACCTTCTGTAAATAACTTTTTTT-GAGAAGGAAATA AAATCAGCTGGAACT-GAACCCTAAAAAAAAAAAAAAAAAAAAAAAAA-AAAAAAAAAAAAGG (SEQ ID NO: 6). However, SOX4 is not limited to the sequence of SEQ ID NO: 6, but rather encompasses other isoforms or variants.

In one embodiment, the biomarker comprises FAM25A. In some embodiments FAM25A may also be referred to as having a GenBank Accession No. of NM_001146157, XM_001723781, XM_002343005, XM_926530, or XM_937048. In one embodiment FAM25A comprises a nucleotide sequence of: TCAGCATCCTAGTTCAC-CACTGTCTGCTGCCACACGATGCTGGGAGGCCTGG GGAAGCTGGCTGCCGAAGGCCTGGCC-CACCGCACCGAGAAGGCCACCGAGG GAGCCATT-CATGCCGTGGAAGAAGTGGT-GAAGGAGGTGGTGGGACACGCCA AGGAGACTGGAGAGAAAGCCATTGCTGAAGCCAT-AAAGAAAGCCCAAGAGT CAGGGGACAAAAAGAT-GAAGGAAATCACTGAGACAGTGAC-CAACACAGTCA CAAATGCCATCACC-CATGCAGCAGAGAGTCTGGACAAACTTGGACAGT-GAGT GCACCTGCTACCACGGCCCTTCCCCAGTCT-CAATAAAAAGCCATGACATGTG TA (SEQ ID NO: 7). However, FAM25A is not limited to the sequence of SEQ ID NO: 7, but rather encompasses other isoforms or variants.

In one embodiment, the biomarker comprises AL832615. In some embodiments AL832615 may also be referred to as having a GenBank Accession No. of AL832615. In one embodiment AL832615 comprises a nucleotide sequence of: GTGGCTCTTGAGCATGGGTGGGGGAAGCCCCCA-CATATCTGAGTCAGTGCCA CCTGGACAC-TACCCTTGGAGCATCCTGCTGAGGTGGCCAT- TCAGGTTTTCTTT CCTTTCCTTTTATTCCACTGTTTGCCTCGGACAT-GAAACATCTCACAGACTGCC TGGAAGAAGGTG-GAGCAGACTGGGGTTAATGGTCAGCAGCAGCAG-CATCCC
CACCACTGGGGCTATCCCTTTTTAGGCCCTTAC-CATGGGCCAAACACTGAGCC
GTGTGCTTCGTGTAACTTCTAAGCACGCTTACCT-GATAGAGTGCCAGCAAAG ACT-CAAAGAGGTGCCTGGGCTTGGCACATAGTAGCTAT-TGCTACTATTATGA
ATGTTGTTTTGTCTTTGTTTTTGTTTTGA-GACAGGGCCTCACTCTGTTGCCCAG GTTGGAGTA-CAGCAGTGCCATCATGGCTCACTGAGGCCT-CAACCTCCCTGGG
TTTGGGCAGTCCTCCCGCCTCGGCCTCCCGAGT-GGCTGGGACTACAGGTGTGC GCCAC-CAAGCCCGGCCGGTTTTTTGTATTTTCAGTAGA-GACTGGTTTTGCCAA
GTCGCCCAGGCTGGTTTCGAACTCTGT-GATCCCAGCACTTTGGGAGGCCGAG GCGGGTG-GATCATGAGGTCAGGAGATCGAGAC-CATCCTGGCTAACAAGGTGA AGC
CCCGTCTCTACTGAAAATACAAAAAAT-TGGCCGGGCGCGGTGGCGGGCG
CCTGTGGTCCCAGCTGCTCGGGAGGCTGAGGCGG-GAGAATGGCGTGAACCCG GGAAGCG-GAGCTTGCAGTGAGCCGAGATTGCGC-CACTGCGGTCCGCAGTCCA
GCCTGGGCGACAGAGCGAGACTCTGTCT-CAAAAAAAAAAAAAAAAAAAAA AATGC-CAAGCTCACCCAGAAATAACCCCGTG-CATATATGGTCAACAGATCTT
TGACAAGGCCATCAAGGATATACAATGTAGAT-TCTTTTATTCCTTTACTTTCTT AATAGACTTGCTTT-CACTGTACTGTAAAAAAAAAAAAGGCACAATGT-AGAAA GGAAACTCTCTTCAATGAATGGTGTTGGG-GAAAGTGCATGAAAAAGAATGAA
ATTGCACACTTGTTTTACATCATATACAGAAAATT-AGCTCAAAGTGGATTAAAGATTTAAATGTAATATCT-GAAACCATGTAAATCCTGGAAGTAAACATAGGGA
AAAATCTCCTCGACATTGGTCATAATTGCAATAT-TTTTTTTGATGTAACACC
AAAGCACAGGCAACAAAAGT-GAAAATAAATAAATGGGACTACATCAATCTT
AAAAGGTTTTACACAGCAAAGGAAAC-CATGACAAAATGAAAAGGCAACCTA CGGGATG-GAAGAAAATATTTGCGACCCATATATTTGA-TAAGGGGTTATTTGA
AAAAATATAAGGAATTCACACAATT-CAATAGCAAAAATTAATAAATACATGA
ATAACGCAATTAAAAATAGGCAAAGGACCC-CAATGGACTTTTTTCCCCAAGG AAGATATA-CAAATGGCCAGCCAGCATATGAAAAGGTGCT-CAACACCACTAAT
CATCAGAGAAATGCAAATCAAAACCACAGTGAGA-TATTGCCTCATAGGGTAG GATGGCTCT-TATAAAAAAACGACAAGAGA-TAACAAGTGTTGGCGAAAGCAT
AGAGGAAAGAGAACCCTTGTACACTGTTGGTTG-GAATGTAAAGTGGTATAAC CTTTA-CAGAAAACAGTATGGAGGTTCCTCAAAAAATT-AGAAGCAGAACTACC
ATACGATTCAGCAATCAGGTTAGAACCTT-GAAGAGAGATCTGCGCCCCATGT TTATTACAACAC-TATTCACAATACCCAAGATATG-GAAACAGCCTAAGTGTCC AGCAACAGATGAATGGATAAATAAAATA-CATATAAACAATGGACTATTAGCC ATT-CAAAAGAAGAAACTCCTGTCCTGGATAAACCTG-GAGGACATTACGCTAA
GTGAAATAAGCCAGACACCGAAA-GACAAGTTTTGTATGATCTCACTTATATG TGG-GATCTAAGAGAGTCAAACTCATAAAAACAGA-TAGTAGAATGGTGGTTGC
CAAGGGCTGGAGGTGGGGAAAATGGGAAGCTAT-TAATCAAAGGGTGTAAAC TTTCAGTTATAAGAT-GAACAAATTCTGGAGATTTAATGTACAGCAT-AGGTGGT
AATGGATGTAATAAATTTGATTGTGATAATTAGTA-CACAATATATACATATAT GAAATCATCACATTGTATG-CATTAAATATACACAATCCTTGTCAACTCAATAT
TTTTAAAAAAATGTTTAAAATGCCTAGGTCAT-AAGAATTCTGAGAATGAAAT ACAACAACATACAT-GAATGGACCTGCTA-CACAGAAGGTGCTAAATAGGTTTG
TTTTGTTTTATTTTATTTCAACTCTGGCAGATGTA-GACCTATTGGGAAAGAAT
ATAGAATGCACTTGTGCACAAGGATTATCTATAC-GATGGTTAAATATCCTGCA TACATGCCATGTCAT-TTCTACTCCTCAGTCAATGGA-TAATAAAAGCAGAACCA
GCTTCTGGTGGTCACAAAACATTTTGACAT-GAGAAAGGCTGATCATGAGCA ATCTGGCAATGTA-CATCCCAGAGCGTGCATGCCCTTTGACCCACAGC-TACCAT
GATGTCATGTCTAGCAATTAGTCCTAAGGAGAT-GATCAGAGATGTGTAAAGA GATTTCATTCTAACAG-CATCCTCTGTAGTGGTATATGTCAGGGGCTGGTA-AGC CATGTCCAGAGGAGCAGGCTGCATCTGGTC-CACCACCTGTTTTTGTAAAGTTT
ATCAGAACACAGTCATGCCCATTCATTTACAAAT-TGTGTATGGCTTCTTTCCC TGCAACAGCAGAGTT-GAGTGTTGCAACAGAAACC-TATGGCCTGCAGAGTTTA
AAATATCTACCCTTTGGCCTTTTATAAAAAAAGTT-TACTGATTCCTGGTGAGT ATATTAAAAGTTAG-GAAAACCTAAATCTTCCAGAGTGGAGAATT-AGAAAGT
AAGCGTGTTGTATATAAGACA-GACAGTTTGTGTGTGCGTTTATTTATAAATA TATTAT-TTTGAAATAATGTTGTCGACATATGTTGCAGGTCT-TAAAAATTGGTC
AATATATAGTGTTAATCAAAAAATGGCAAAT-TGTAAAATGTAGACAGAATGT GATTGTGTAT-TTTGTGCATACACCAACAGAAAAGGGTGCTAG-GAAACCTGTG
GACCAACATACTAAGTGTGGCTCTTTT-GATGGTGGTATCATGGATTTTAAAA ATCTTCTTGGTTTTCTGTAGAT-TCTGACTTTCCTGTAATGAGTATGAATAAGTA TGT-ATTTCTTGAGAAATGAGAAAATAACTT-TATCTTCCCAGATTTCTCATAAT
TGAAAATGTTGGAATAAATGGTCCTGGGACA-GATCTTTCCATTGAGAAGGGC GGAAGG-GAAACCCTGGGGATTCAGCTGGGTTTCTGTTGCAT-TTCTGGTAACA
CACAGTTGTGAAAAGCCAGTGTTGGCCAT-TCCCCAGGACAGTCTGGGGTAGA GGAGGTCAG-GATTTAACTACTTGAGGGTCCGGGGAACA-GATGTGGCCACAGT
CCTTCCTGACTCACTGTTTTCCCTTC-CACAGTCCCGTCTTCTCTTCACTGATG CACATA-GATGCCTGACCAGAGGAGAGATTTAGTTTTCGTC- CAAGGATTATCT GTTATGTTGCAGTTCTGAAATTCCCATAACGTT-TAGGCTAGAACACAAGTGAT TTCATTATCTC-CAATGTGTATGGCTTGATAGAAATAGATTCCAT-TATGTAGCA CCTTAAATCCAGATAAAACATAAGGAATTTCTATTC-CATGTTTGTATGATCAA TGT-TAATAATCTAAGAAAATCTAAAAAGAAGC-TACTTCCTCTATTACAGTATG AAATAAATATGCTGAATGATTTGTCTTGGGGGGTG-GAATGGAAAGGTATAAG ACTGAG-GAGGGTGCCTGTGGGAACAGTGATAG-GAATCCTTTCTTAAGGGTTG GGTTTTACATACGTCTTTTAAAATAGATGATATCAT-TAATAAATTATCTGTGG GCATCAT-GAAAAAAGTGTATAACGTACAACTTTAT-GAGCTTGACAGTTGGTG AAAACTTTTCTGTTTAAAATTTTATTTGGCCCTCCC-CAAAAGAAATGTTTATTT ATGAGTATTAGGA-TAGTTCCAGCAGTAATGCCTCAAAAGAACCAG-GAGGTAT AGTGTTGTCTAAAATGTGGACTCAGGAGCCA-GACTGCCTGGCTGTGCAACTA GCCTTGT-CACTTCCTAGATATGTGGCAAGTTAAT-TAACTTCTCAGTGTTCTTAT CTGTAGAATGGGGATAATCCTAATATA-CATCTCAGGGTTATATTACAAATTTG AGAAGTTAAT-TTTGTAAAGGACTTAGAATGA-TATCTGGCAAATAAAAGTGTT CATAAAAGCAAAAAAA (SEQ ID NO: 8). However, AL832615 is not limited to the sequence of SEQ ID NO: 8, but rather encompasses other isoforms or variants.

In one embodiment, the biomarker comprises SLPI. In some embodiments SLPI may also be referred to as having a GenBank Accession No. of NM 003064 in one embodiment SLPI comprises a nucleotide sequence of: CAGAGT-CACTCCTGCCTTCACCAT-GAAGTCCAGCGGCCTCTTCCCCTTCCTGG TGCTGCTTGCCCTGG-GAACTCTGGCACCTTGGGCTGTGGAAGGCTCTG-GAAA GTCCTTCAAAGCTG-GAGTCTGTCCTCCTAAGAAATCTGCCCAGTGCCT-TAGAT ACAAGAAACCT-GAGTGCCAGAGTGACTGGCAGTGTCCAGG-GAAGAAGAGAT GTTGTCCTGACACTTGTGGCAT-CAAATGCCTGGATCCTGTTGACACCCCAAAC CCAACAAGGAGGAAGCCTGG-GAAGTGCCCAGTGACTTATGGCCAATGTTTGA TGCTTAACCCCCCCAATTTCTGTGAGATG-GATGGCCAGTGCAAGCGTGACTTG AAGTGTTG-CATGGGCATGTGTGG-GAAATCCTGCGTTTCCCCTGTGAAAGCTTG ATTCCTGCCATATGGAGGAGGCTCTG-GAGTCCTGCTCTGTGTGGTCCAGGTCC TTTC-CACCCTGAGACTTGGCTCCACCACTGA-TATCCTCCTTTGGGGAAAGGCT TGGCACACAGCAGGCTTTCAAGAAGTGCCAGTT-GATCAATGAATAAATAAAC GAGCCTAT-TTCTCTTTGCAC (SEQ ID NO: 9). However, SLPI is not limited to the sequence of SEQ ID NO: 9, but rather encompasses other isoforms or variants.

In one embodiment, the biomarker comprises CRCT1. In some embodiments CRCT1 may also be referred to as having a GenBank Accession No. of NM_019060, In one embodiment CRCT1 comprises a nucleotide sequence of: GCCCATTCCAGTTGGAGAACGTAGT-GAGTCTTTCAGTGGAGCCAGGGTCTGG TTTGTCGTGAGGAGCTCCGCGATGTCCTCT-CAACAGAGCGCCGTTTCCGCCAA AGGCTTTTC-CAAGGGGTCGTCCCAGGGCCCCGCTCCGTGTCC-CGCCCCGGCG CCCACCCCGGCGCCCGCCTCCTCCTCCTGC-TGCGGCTCCGGCAGGGGCTG CTGCGGCGACTCAGGCTGCTGCGGCTCCAGCTC-CACCAGTTGCTGCTGCTTCC CAAGGA-GACGCCGCCGACAGCG-GAGTAGTGGTTGCTGCTGCTGCGGGGGCG GCAGCCAGAGGTCCCAGCGCTCCAACACCG-GAGCTCAGGATGCTGCTCCGG CTGCT-GAGAGGCCCGCAACCCCCAGCGCTGCGCTAG-AGAAACCCGCCCAGCC CAGAGCGGGCCCGCCCCGCTGCGGCTCC-CACGCGGGGCTGGGCCTCGGAGTT TGCCCCGTAAAGCGAATTGCACTTT-GATGTTCAGAAACCCACTTTGTTCTCAG CCACGCAAAACTCCCTGACCCCGATGTGAT-TTTTCTCCCCGGGGATTCGAGAG CCATGCGTGGGACACTGGACCCTACTGTCTA-CACGGGCTTGCACACAGCAGG TGCTCAGCAAATGTCTATTGATTTGATTGTCTTTT-GAAGATGTCATAATAAAG CTTCTACCTCCT-GAAAAA (SEQ ID NO: 10). However, CRCT1 is not limited to the sequence of SEQ ID NO: 10, but rather encompasses other isoforms or variants.

Identifying a Marker or Biomarker

The invention includes methods for the identification of markers differentially expressed between samples of healthy subjects and subjects with gingivitis. In some embodiments, the invention includes methods for identification of markers differentially expressed between samples obtained over time from a subject being monitored or treated with a gingivitis treatment.

The invention contemplates the identification of differentially expressed markers by whole genome nucleic acid microarray, PCR, or immunoassay. The invention further contemplates using methods known to those skilled in the art to detect and to measure the level of differentially expressed marker expression products, such as RNA and protein, to measure the level of one or more differentially expressed marker expression products.

Methods of detecting or measuring gene expression may utilize methods that focus on cellular components (cellular examination), or methods that focus on examining extracellular components (fluid examination). Because gene expression involves the ordered production of a number of different molecules, a cellular or fluid examination may be used to detect or measure a variety of molecules including RNA, protein, and a number of molecules that may be modified as a result of the protein's function. Typical diagnostic methods focusing on nucleic acids include amplification techniques such as PCR and RT-PCR (including quantitative variants), and hybridization techniques such as in situ hybridization, microarrays, blots, and others. Typical diagnostic methods focusing on proteins include binding techniques such as ELISA, immunohistochemistry, microarray and functional techniques such as enzymatic assays.

The genes identified as being differentially expressed may be assessed in a variety of nucleic acid detection assays to detect or quantify the expression level of a gene or multiple genes in a given sample. For example, traditional Northern blotting, nuclease protection, RT-PCR, microarray, and differential display methods may be used for detecting gene expression levels. Methods for assaying for mRNA include Northern blots, slot blots, dot blots, and hybridization to an ordered array of oligonucleotides. Any method for specifically and quantitatively measuring a specific protein or mRNA or DNA product can be used. However, methods and assays are most efficiently designed with array or chip hybridization-based methods for detecting the expression of a large number of genes. Any hybridization assay format may be used, including solution-based and solid support-based assay formats.

The protein products of the genes identified herein can also be assayed to determine the amount of expression. Methods for assaying for a protein include Western blot, immunoprecipitation, and radioimmunoassay. The proteins analyzed may be localized intracellularly (most commonly an application of immunohistochemistry) or extracellularly (most commonly an application of immunoassays such as ELISA).

Biological samples may be of any biological tissue or fluid containing saliva. Frequently the sample will be a "clinical sample" which is a sample derived from a patient. The biological sample may contain any biological material suitable for detecting the desired biomarkers, and may comprise cellular and/or non-cellular material obtained from the individual. One example of a biological sample is a whole saliva sample. Another example of a biological sample is a cell-free saliva sample. Another example of a biological sample is a saliva supernatant, such as the supernatant obtained after centrifuging a saliva sample. Another example of a biological sample is the material in a pellet obtained from a saliva sample, such as a pellet obtained after centrifuging a saliva sample (i.e., saliva pellet). In another example, the biological sample is the pellet obtained from centrifuging another biological sample, including, but not limited to, blood, gingival crevicular fluid, and the like.

Controls group samples may either be from normal subject or samples from subjects with a known severity of gingivitis. In some embodiments a control sample is a baseline sample obtained from a subject before a treatment regimen is initiated. In some embodiments, a control sample is a sample obtained from a subject at an earlier time point.

As described below, comparison of the expression patterns of the sample to be tested with those of the controls can be used to diagnose gingivitis, monitor gingivitis, or evaluate the response to gingivitis treatment. In some instances, the control groups are only for the purposes of establishing initial cutoffs or thresholds for the assays of the invention. Therefore, in some instances, the systems and methods of the invention can diagnose gingivitis without the need to compare with a control group.

Methods of Diagnosis

The present invention relates to the identification of biomarkers associated with gingivitis. Accordingly, the present invention features methods for identifying subjects having gingivitis, or who are at risk of developing gingivitis, including those subjects who are asymptomatic or only exhibit non-specific indicators of gingivitis by detection of the biomarkers disclosed herein.

These biomarkers are also useful for monitoring subjects undergoing treatments and therapies for gingivitis, and for selecting or modifying therapies and treatments that would be efficacious in subjects having gingivitis, wherein selection and use of such treatments and therapies slow the progression of gingivitis, or prevent its onset.

The invention provides improved methods for the diagnosis and prognosis of gingivitis. The risk of developing gingivitis can be assessed by measuring one or more of the biomarkers described herein, and comparing the measured values to comparator values, reference values, or index values. Such a comparison can be undertaken with mathematical algorithms or formula in order to combine information from results of multiple individual biomarkers and other parameters into a single measurement or index. Subjects identified as having an increased risk of gingivitis can optionally be selected to receive treatment regimens, such as prophylactic or therapeutic agents, dental procedures, periodontal procedures, or oral hygiene counseling to prevent, treat or delay the onset of gingivitis.

Identifying a subject before they develop gingivitis enables the selection and initiation of various therapeutic interventions or treatment regimens in order to delay, reduce or prevent that subject's conversion to a disease state. Monitoring the levels of at least one biomarker also allows for the course of treatment of gingivitis to be monitored. For example, a sample can be provided from a subject undergoing treatment regimens or therapeutic interventions for gingivitis. Such treatment regimens or therapeutic interventions can include administration of pharmaceuticals, therapeutics or prophylactics; professional dental cleaning; scaling and root planning; use of chlorohexidine rinses; use of toothpastes containing Stannous, Zinc, Triclosan, and/or hydrogen peroxide; use of mouthwashes containing Triclosan, Cetylpyridinium chloride, other quats (e.g., BKC) and/or essential oils; and at-home oral hygiene regimens. Samples can be obtained from the subject at various time points before, during, or after treatment.

The biomarkers of the present invention can thus be used to generate a biomarker profile or signature of the subjects: (i) who do not have and are not expected to develop gingivitis and/or (ii) who have or expected to develop gingivitis. The biomarker profile of a subject can be compared to a predetermined or comparator biomarker profile or reference biomarker profile to diagnose or identify subjects at risk of developing gingivitis, to monitor the progression of disease, as well as the rate of progression of disease, and to monitor the effectiveness of treatments. Data concerning the biomarkers of the present invention can also be combined or correlated with other data or test results, such as, without limitation, measurements of clinical parameters or other algorithms for gingivitis. Other data includes gender, age, ethnicity, height, weight, diet, genetics, smoking, mouth-breathing, mouth-breathing during sleep, obesity, heart disease, osteoporosis, hypertension, diabetes, bowel diseases, muscle and joint disease, tumor, mental illness, caries, missing teeth, level of oral hygiene, level of dental care utilization, and use of medications that dry the mouth, and the like. In some embodiments, the data includes results of one or more assays for gingivitis, including, but not limited to Loe-Silness Gingival Index (GI), Quigley and Hein Plaque Index (PI), Turesky-modification of the Quigly and Hein index, gingival bleeding index, Navy index, modified Navy index, bleeding on probing (BOP), and probing depth (PD). The data can also comprise subject information such as medical history and any relevant family history.

The present invention also provides methods for identifying agents for treating or preventing gingivitis that are appropriate or otherwise customized for a specific subject. In this regard, a test sample from a subject, exposed to a therapeutic agent or a drug, can be taken and the level of one or more biomarkers can be determined. The level of one or more biomarkers can be compared to a sample derived from the subject before and after treatment, or can be compared to samples derived from one or more subjects who have shown improvements in risk factors as a result of such treatment or exposure.

In various embodiments, methods are disclosed herein that may be of use to determine whether a subject has gingivitis. In some embodiments, these methods may utilize a biological sample (such as urine, saliva, blood, serum, amniotic fluid, gingival crevicular fluid, or tears), for the detection of one or more markers of the invention in the sample.

In one embodiment, the biomarker for the detection of gingivitis, includes but is not limited to at least one of NONHSAT006501.2, NONHSAT071649, NONHSAT005224, LGALS3, AF156166, SOX4, FAM25A, AL832615, SLPI, and CRCT1.

In one embodiment, the method comprises detecting that at least one biomarker selected from NONHSAT071649, NONHSAT005224, AF156166, and SOX4 is upregulated as compared to a comparator control. For example, in one embodiment, the method comprises detecting that the level of at least one biomarker selected from NONHSAT071649, NONHSAT005224, AF156166, and SOX4 is increased as compared to the level of the at least one biomarker in a comparator control.

In one embodiment, the method comprises detecting that at least one biomarker selected from NONHSAT006501.2, LGALS3, FAM25A, and CRCT1 is downregulated as compared to a comparator control. For example, in one embodiment, the method comprises detecting that the level of at least one biomarker selected from NONHSAT006501.2, LGALS3, FAM25A, and CRCT1 is decreased as compared to the level of the at least one biomarker in a comparator control.

In one embodiment, the method comprises detecting one or more markers in a biological sample of the subject. In one embodiment, the biological sample is saliva. In various embodiments, the level of one or more of markers of the invention in the biological sample of the subject is compared with the level of the biomarker in a comparator. Non-limiting examples of comparators include, but are not limited to, a negative control, a positive control, standard control, standard value, an expected normal background value of the subject, a historical normal background value of the subject, a reference standard, a reference level, an expected normal background value of a population that the subject is a member of, or a historical normal background value of a population that the subject is a member of.

In another embodiment, the invention is a method of monitoring the progression or regression of gingivitis in a subject by assessing the level of one or more of the markers of the invention in a biological sample of the subject. In one embodiment, the invention provides a method of monitoring the response of a gingivitis treatment in a subject by assessing the level of one or more of the markers of the invention in a biological sample of the subject.

In one embodiment, the invention provides determining that gingivitis is regressing in a subject by detecting that at least one biomarker selected from NONHSAT071649, NONHSAT005224, AF156166, and SOX4 is downregulated as compared to a comparator control. For example, in one embodiment, the method comprises detecting that the level of at least one biomarker selected from NONHSAT071649, NONHSAT005224, AF156166, and SOX4 is decreased as compared to the level of the at least one biomarker in a comparator control.

In one embodiment, the invention provides determining that gingivitis is regressing in a subject by detecting that at least one biomarker selected from NONHSAT006501.2, LGALS3, FAM25A, and CRCT1 is upregulated as compared to a comparator control. For example, in one embodiment, the method comprises detecting that the level of at least one biomarker selected from NONHSAT006501.2, LGALS3, FAM25A, and CRCT1 is increased as compared to the level of the at least one biomarker in a comparator control.

In one embodiment, the invention provides determining that a subject is responsive to a gingivitis treatment by detecting that at least one biomarker selected from NONHSAT071649, NONHSAT005224, AF156166, and SOX4 is downregulated as compared to a comparator control. For example, in one embodiment, the method comprises detecting that the level of at least one biomarker selected from NONHSAT071649, NONHSAT005224, AF156166, and SOX4 is decreased as compared to the level of the at least one biomarker in a comparator control.

In one embodiment, the invention provides determining that a subject is responsive to a gingivitis treatment by detecting that at least one biomarker selected from NONHSAT006501.2, LGALS3, FAM25A, CRCT1 is upregulated as compared to a comparator control. For example, in one embodiment, the method comprises detecting that the level of at least one biomarker selected from NONHSAT006501.2, LGALS3, FAM25A, CRCT1 is increased as compared to the level of the at least one biomarker in a comparator control.

In some embodiments, the comparator control is a baseline level of the one or more biomarkers, for example the baseline level of the one or more biomarkers obtained prior to the initiation of the treatment. In some embodiments, the comparator control is the level of one or more biomarkers in a sample obtained at an earlier time point in the treatment regimen.

In various embodiments, the subject is a human subject, and may be of any race, sex and age.

Information obtained from the methods of the invention described herein can be used alone, or in combination with other information (e.g., disease status, disease history, vital signs, blood chemistry, etc.) from the subject or from the biological sample obtained from the subject.

In various embodiments of the methods of the invention, the level of one or more markers of the invention is determined to be increased when the level of one or more of the markers of the invention is increased by at least 10%, by at least 20%, by at least 30%, by at least 40%, by at least 50%, by at least 60%, by at least 70%, by at least 80%, by at least 90%, or by at least 100%, when compared to with a comparator.

In other various embodiments of the methods of the invention, the level of one or more markers of the invention is determined to be decreased when the level of one or more of the markers of the invention is decreased by at least 10%, by at least 20%, by at least 30%, by at least 40%, by at least 50%, by at least 60%, by at least 70%, by at least 80%, by at least 90%, or by at least 100%, when compared to with a comparator.

In the methods of the invention, a biological sample from a subject is assessed for the level of one or more of the markers of the invention in the biological sample obtained from the patient. The level of one or more of the markers of the invention in the biological sample can be determined by assessing the amount of polypeptide of one or more of the biomarkers of the invention in the biological sample, the amount of RNA of one or more of the biomarkers of the invention in the biological sample, the amount of enzymatic activity of one or more of the biomarkers of the invention in the biological sample, or a combination thereof.

Detecting a Biomarker

In one embodiment, the invention includes detecting an RNA in a bodily fluid, wherein the bodily fluid is saliva and the RNA is detected in saliva. In another embodiment, the invention includes detecting an extracellular RNA in a bodily fluid, wherein the bodily fluid is saliva and the extracellular RNA is detected in a cell-free fluid phase portion of saliva. In some embodiments, detection of mRNAs is performed in a portion of saliva (e.g., supernatant, cell-free fluid phase) wherein presence of microorganisms and the extraneous substances such as food debris is minimized, which allows analyzing the molecules in simple and accurate fashion. In some embodiments, the cell-free fluid phase portion of derived from unstimulated saliva.

In one embodiment, detecting extracellular RNAs herein also informative RNAs, is performed in a bodily fluid, saliva, that meets the demands of an inexpensive, noninvasive and accessible bodily fluid to act as an ideal medium for investigative analysis.

Biomarkers generally can be measured and detected through a variety of assays, methods and detection systems known to one of skill in the art. Various methods include but are not limited to refractive index spectroscopy (RI), ultraviolet spectroscopy (UV), fluorescence analysis, electrochemical analysis, radiochemical analysis, near-infrared spectroscopy (near-IR), infrared (IR) spectroscopy, nuclear magnetic resonance spectroscopy (NMR), light scattering analysis (LS), mass spectrometry, pyrolysis mass spectrometry, nephelometry, dispersive Raman spectroscopy, gas chromatography, liquid chromatography, gas chromatography combined with mass spectrometry, liquid chromatography combined with mass spectrometry, matrix-assisted laser desorption ionization-time of flight (MALDI-TOF) combined with mass spectrometry, ion spray spectroscopy combined with mass spectrometry, capillary electrophoresis, colorimetry and surface plasmon resonance (such as according to systems provided by Biacore Life Sciences). See also PCT Publications WO/2004/056456 and WO/2004/088309. In this regard, biomarkers can be measured using the above-mentioned detection methods, or other methods known to the skilled artisan. Other biomarkers can be similarly detected using reagents that are specifically designed or tailored to detect them.

Different types of biomarkers and their measurements can be combined in the compositions and methods of the present invention. In various embodiments, the protein form of the biomarkers is measured. In various embodiments, the nucleic acid form of the biomarkers is measured. In exemplary embodiments, the nucleic acid form is RNA. In various embodiments, measurements of protein biomarkers are used in conjunction with measurements of nucleic acid biomarkers.

Methods for detecting mRNA, such as RT-PCR, real time PCR, branch DNA, NASBA and others, are well known in the art. Using sequence information provided by the database entries for the biomarker sequences, expression of the biomarker sequences can be detected (if present) and measured using techniques well known to one of ordinary skill in the art. For example, sequences in sequence database entries or sequences disclosed herein can be used to construct probes for detecting biomarker RNA sequences in, e.g., Northern blot hybridization analyses or methods which specifically, and in some instances, quantitatively, amplify specific nucleic acid sequences. As another example, the sequences can be used to construct primers for specifically amplifying the biomarker sequences in, e.g., amplification-based detection methods such as reverse-transcription based polymerase chain reaction (RT-PCR). When alterations in gene expression are associated with gene amplification, deletion, polymorphisms and mutations, sequence comparisons in test and reference populations can be made by comparing relative amounts of the examined DNA sequences in the test and reference cell populations. In addition to Northern blot and RT-PCR, RNA can also be measured using, for example, other target amplification methods (e.g., TMA, SDA, NASBA), signal amplification methods (e.g., bDNA), nuclease protection assays, in situ hybridization and the like.

The concentration of the biomarker in a sample may be determined by any suitable assay. A suitable assay may include one or more of the following methods, an enzyme assay, an immunoassay, mass spectrometry, chromatography, electrophoresis or an antibody microarray, or any combination thereof. Thus, as would be understood by one skilled in the art, the system and methods of the invention may include any method known in the art to detect a biomarker in a sample.

The invention described herein also relates to methods for a multiplex analysis platform. In one embodiment, the method comprises an analytical method for multiplexing analytical measurements of markers. In another embodiment, the method comprises a set of compatible analytical strategies for multiplex measurements of markers and/or metabolites in saliva.

Kits

The present invention also pertains to kits useful in the methods of the invention. Such kits comprise various combinations of components useful in any of the methods described elsewhere herein, including for example, materials for quantitatively analyzing a biomarker of the invention (e.g., polypeptide and/or nucleic acid), materials for assessing the activity of a biomarker of the invention (e.g., polypeptide and/or nucleic acid), and instructional material. For example, in one embodiment, the kit comprises components useful for the quantification of a desired nucleic acid in a biological sample. In another embodiment, the kit comprises components useful for the quantification of a desired polypeptide in a biological sample. In a further embodiment, the kit comprises components useful for the assessment of the activity (e.g., enzymatic activity, substrate binding activity, etc.) of a desired polypeptide in a biological sample.

In a further embodiment, the kit comprises the components of an assay for monitoring the effectiveness of a treatment administered to a subject in need thereof, containing instructional material and the components for determining whether the level of a biomarker of the invention in a biological sample obtained from the subject is modulated during or after administration of the treatment. In various embodiments, to determine whether the level of a biomarker of the invention is modulated in a biological sample obtained from the subject, the level of the biomarker is compared with the level of at least one comparator control contained in the kit, such as a positive control, a negative control, a historical control, a historical norm, or the level of another reference molecule in the biological sample. In some embodiments, the ratio of the biomarker and a reference molecule is determined to aid in the monitoring of the treatment.

Treatments

In some aspects, the present invention provides a method for treating a subject diagnosed with gingivitis using one or more of the biomarkers described herein. For example, in one embodiment, the method comprises a method of treating a subject composing detecting that the level of the one or more biomarkers in a saliva sample of the subject is differentially expressed as compared to the level in a comparator control, and administering a gingivitis treatment to the subject. Exemplary treatments administered to the subject include, but is not limited to administration of a therapeutic agent, dental procedures, periodontal procedures, surgical procedures, and communication or training of improved oral hygiene.

Exemplary procedures include, but is not limited to, professional plaque cleaning, scaling, root planning, dental restoration, curettage, flap surgery, bone and tissue grafts, guided tissue regeneration, oral irrigation, interdental brushing and brushing using wooden or plastic pick.

In some embodiments, treatment comprises administering a disease-modulating agent to a subject. The agent can be a therapeutic or prophylactic used in subjects diagnosed or identified with a disease or at risk of having the disease. For example, in some embodiments, the therapeutic or prophylactic agent may be in the form of a toothpaste, mouthwash, dental strips, or other formulations suitable for delivery to the gums. In some embodiments, modifying therapy refers to altering the duration, frequency or intensity of therapy, for example, altering dosage levels. Exemplary therapeutic or prophylactic agents include, but is not limited to, antiseptic and antimicrobial agents, such as triclosan, chlorhexidine, and hydrogen peroxide; plaque reducers; anti-inflammatory agents, such as thymol, menthol, eucalyptol, and methyl salicylate; antibiotic agents, such as minocycline and doxycycline; nonsteroidal anti-inflammatory drugs (NSAIDs); chlorohexidine rinses; toothpastes containing Stannous, Zinc, Triclosan, and/or hydrogen peroxide; and mouthwashes containing Triclosan, Cetylpyridinium chloride, other quats (e.g., BKC) and/or essential oils.

In various embodiments, effecting a therapy comprises causing a subject to or communicating to a subject the need to make a change in lifestyle, for example, improving oral hygiene, more frequent flossing, or more frequent brushing of teeth. The therapy can also include dental procedures, periodontal procedures, or surgery. Exemplary procedures include, but is not limited to, professional plaque cleaning, scaling, root planning, dental restoration, curettage, flap surgery, bone and tissue grafts, guided tissue regeneration, oral irrigation, interdental brushing and brushing using wooden or plastic pick.

Measurement of biomarker levels allow for the course of treatment of a disease to be monitored. The effectiveness of a treatment regimen for a disease can be monitored by detecting one or more biomarkers in an effective amount from samples obtained from a subject over time and comparing the amount of biomarkers detected. For example, a first sample can be obtained prior to the subject receiving treatment and one or more subsequent samples are taken after or during treatment of the subject. Changes in biomarker levels across the samples may provide an indication as to the effectiveness of the therapy.

To identify therapeutics or drugs that are appropriate for a specific subject, a test sample from the subject can also be exposed to a therapeutic agent or a drug, and the level of one or more biomarkers can be determined. Biomarker levels can be compared to a sample derived from the subject before and after treatment or exposure to a therapeutic agent or a drug, or can be compared to samples derived from one or more subjects who have shown improvements relative to a disease as a result of such treatment or exposure. Thus, in one aspect, the invention provides a method of assessing the efficacy of a therapy with respect to a subject comprising taking a first measurement of a biomarker panel in a first sample from the subject; effecting the therapy with respect to the subject; taking a second measurement of the biomarker panel in a second sample from the subject and comparing the first and second measurements to assess the efficacy of the therapy.

Additionally, therapeutic or prophylactic agents suitable for administration to a particular subject can be identified by detecting a biomarker (which may be two or more) in an effective amount from a sample obtained from a subject and exposing the subject-derived sample to a test compound that determines the amount of the biomarker(s) in the subject-derived sample. Accordingly, treatments or therapeutic regimens for use in subjects having a disease or subjects at risk for developing a disease can be selected based on the amounts of biomarkers in samples obtained from the subjects and compared to a reference value. Two or more treatments or therapeutic regimens can be evaluated in parallel to determine which treatment or therapeutic regimen would be the most efficacious for use in a subject to delay onset, or slow progression of a disease. In various embodiments, a recommendation is made on whether to initiate or continue treatment of a disease.

In various exemplary embodiments, effecting a therapy comprises administering a disease-modulating drug to the subject. The subject may be treated with one or more disease-modulating drugs until altered levels of the measured biomarkers return to a baseline value measured in a population not suffering from the disease, experiencing a less severe stage or form of a disease or showing improvements in disease biomarkers as a result of treatment with a disease-modulating drug. Additionally, improvements related to a changed level of a biomarker or clinical parameter may be the result of treatment with a disease-modulating drug.

A number of compounds such as a disease-modulating drug may be used to treat a subject and to monitor progress using the methods of the invention. In some embodiments, the disease-modulating drug comprises antiseptic and antimicrobial agents, such as triclosan, chlorhexidine, and hydrogen peroxide; plaque reducers; anti-inflammatory agents, such as thymol, menthol, eucalyptol, and methyl salicylate; antibiotic agents, such as minocycline and doxycycline; and nonsteroidal anti-inflammatory drugs (NSAIDs).

The beneficial effects of these and other drugs can be visualized by assessment of clinical and laboratory biomarkers.

Any drug or combination of drugs disclosed herein may be administered to a subject to treat a disease. The drugs herein can be formulated in any number of ways, often according to various known formulations in the art or as disclosed or referenced herein.

In various embodiments, any drug or combination of drugs disclosed herein is not administered to a subject to treat a disease. In these embodiments, the practitioner may refrain from administering the drug or combination of drugs, may recommend that the subject not be administered the drug or combination of drugs or may prevent the subject from being administered the drug or combination of drugs.

In various embodiments, one or more additional drugs may be optionally administered in addition to those that are recommended or have been administered. An additional drug will typically not be any drug that is not recommended or that should be avoided.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore are not to be construed as limiting in any way the remainder of the disclosure.

Example 1: Salivary exRNA Biomarkers to Detect Gingivitis and Monitor Disease Regression Extracellular RNAs (exRNAs) are emerging molecular targets as biomarkers in bodily fluids that can be useful biomarkers for the disease detection and monitoring. The NIH's Extracellular RNA Communication Consortium (ERCC) credentialed the existence, the biology and the translational utilities of exRNA in bodily fluids, including saliva (Ainsztein et al., 2015, J Extracell Vesicles 4, 27493). The human salivary transcriptome was firstly described in 2004 (Li et al., 2004, J Dent Res, 83, 199-203) followed by the intense investigations in the following years (Nussbaumer et al., 2006, Forensic Sci Int, 157, 181-6). Inflammatory mRNA markers can be detected in whole saliva to monitor the status of periodontal disease in type II diabetes patients (Gomes et al., 2006, J Periodontal Res., 41, 177-83). mRNA expression of human beta defensin-1 and-2 in the gingival tissue are associated with gingivitis, aggressive and chronic periodontitis. Also, the expression levels of Toll-like receptors (TRL) TRL7, TRL9, IFN-alpha1 messenger RNAs (mRNAs) (Kajita et al., 2007, Oral Microbiol Immunol, 22, 398-402) and MYD88 mRNA (Ghaderi et al., 2014, J Indian Soc Periodontol., 18, 150-154) were significantly lower in gingivitis than in periodontitis lesions. In addition, four miRNAs (hsa-miR-451, hsa-miR-223, hsa-miR-486-5p, hsa-miR-3917) were significantly overexpressed, and 7 (hsa-miR-1246, hsa-miR-1260, hsa-miR-141, hsa-miR-1260b, hsa-miR-203, hsa-miR-210, hsa-miR-205) were underexpressed by >2-fold in gingivitis compared to healthy gingiva (Stoecklin-Wasmer et al., 2012, J Dent Res., 91, 934-40). However, not much evidence can be found in the literature about the long non-coding (lnc) RNAs as biomarkers for periodontal diseases (Wang et al., 2016, *Cell Death Dis.*, 7, e2327), especially for gingivitis as it is yet a new and a flourishing field. Bochenek et al., reports about the downregulation of large non-coding RNA ANRIL associated with atherosclerosis, periodontitis and several forms of cancer (Bochenek et al., 2013, Hum Mol Genet. 22, 4516-27).

The experiments presented herein were conducted to examine whether salivary extracellular RNA (exRNA) biomarkers can be developed for gingivitis detection and monitoring disease progression or regression. Salivary exRNA biomarker candidates were developed from a total of 100 gingivitis and non-gingivitis human participants using Affymetrix's expression microarrays. In the study design, the diagnosis of gingivitis fulfilled both clinical and research criteria. The top ten differentially expressed exRNAs were tested in a clinical cohort to determine if the discovered salivary exRNA markers for gingivitis were associated with clinical gingivitis and disease progression/regression. For this purpose, unstimulated saliva was collected from 30 randomly selected gingivitis subjects, the gingival and plaque indexes scores were taken at baseline, 3 & 6 weeks and salivary exRNAs were assayed by means of quantitative reverse transcription polymerase chain reaction. It is demonstrated herein that 8 out of 10 salivary exRNA biomarkers developed for gingivitis were statistically significantly changed over time, consistent with disease regression. A panel of four of the eight salivary exRNAs [NONHSAT006501.2; NONHSAT071649; FAM25A; NM_019060] can detect gingivitis with a clinical performance of 0.91 AUC (area under the curve) with 71% sensitivity and 100% specificity. The experiments described herein demonstrate that salivary exRNA biomarkers for gingivitis detection have been developed. Their clinical values and utilities have been demonstrated in a pilot clinical study and are associated with gingivitis regression. These salivary exRNAs offer strong potential to be advanced for definitive validation and clinical laboratory development test (LDT). This study addresses the unmet clinical need of assessing host factors as a companion diagnostics to detect gingivitis, which can be treated clinically or therapeutically to halt disease progress and/or regress to a healthy periodontium.

The materials and methods used in these experiments are now described.

Discovery Phase

Based on the PRoBE (prospective-specimen-collection and retrospective-blinded-evaluation) study design (Pepe et al., 2008), saliva was collected prospectively from 750 human subjects. Subjects were classified as healthy or gingivitis according to research and clinical criteria. Research criteria consisted of evaluation of marginal bleeding index (MBI) and pocket depth (PD) as follows: 1) Healthy (non-periodontal disease): MBI<5%; PD<4 mm; 2) Gingivitis: MBI>5%; PD<4 mm. Clinical criteria were assessed by examination of the entire dentition for six sites per tooth (mesio-buccal, mid-buccal, disto-buccal, mesio-lingual, mid-lingual, and disto-lingual). In addition, the following parameters were assessed in a full-mouth evaluation: pocket probing depths, presence/absence of bleeding upon probing, plaque index and marginal bleeding index, visual signs of gingival tissue inflammation and radiographic bone levels. The clinical classification of a subject's periodontal status (i.e. healthy, gingivitis) was a cumulative assessment of objective evaluations and clinical judgment that presents a holistic assessment of a subject's periodontal status.

In addition, in order to be included in the study, all subjects must have had at least 20 teeth and could not have received periodontal treatment or antibiotic therapy three months prior to the investigation. The volunteers did not previously undergo any long-term use of medications affecting periodontal status such as anti-inflammatory drugs. Subjects were excluded if they were smokers, possessed a history of metabolic bone diseases, autoimmune diseases, unstable diabetes or post-menopausal osteoporosis. Women who were pregnant were not included.

All saliva samples were treated for the concurrent stabilization of proteins and RNA by the inclusion of a protease inhibitor cocktail (aprotinin, PMSF and sodium orthovanadate) and RNase inhibitor (SUPERase•In; Ambion, Austin Tex.) based on a saliva standard operating procedure (SOP) (Henson et al., 2010). Salivary exRNA was extracted using the RNeasy Micro Kit (Qiagen) including DNase I digestion. Samples with good purity QC (OD 260/280~1.8) were profiled using the GeneChip Human Transcriptome Affymetrix HTA 2.0 expression arrays. The salivary exRNA biomarker candidates were identified from a discovery cohort of 50 gingivitis and 50 age/gender-matched control subjects with healthy periodontium. The top 10 differentially expressed exRNA biomarker candidates between gingivitis and healthy groups were advanced for validation by means of quantitative reverse transcription polymerase chain reaction (qRT-PCR) using an independent cohort of 30 randomly selected gingivitis subjects in the pilot clinical research study.

Pilot Clinical Research Study

Clinical Stage

For analysis of saliva samples, 30 volunteers (aged 18-65), diagnosed with gingivitis were included in this study. The duration of this project was 7 weeks (including 1 week pretrial washout period) and included treatment of gingivitis by brushing with toothpastes. The inclusion criteria encompassed: good general health, presence of ≥20 natural uncrowned teeth (excluding third molars), no history of allergy to personal care consumer products, or their ingredients, initial gingivitis index of at least 1.0 as determined by the Löe-Silness Gingival Index (GI) (Löe, 1967, Journal of Periodontology, 38, 610-616) and initial plaque index of at least 1.5 as determined by the Quigley and Hein Plaque Index (PI) (Turesky Modification) (Quigley & Hein, 1962, JADA, 65, 26-29; Turesky et al., 1970, J. Periodontol, 41, 41-43). None of the individuals had a history of any medical condition, which required pre-medication or the presence of any pocket equal or deeper than 5 mm (except for 3rd molars). Other exclusion criteria involved five or more carious lesions, other disease of the hard or soft oral tissues, impaired salivary function, use of medications that can currently affect salivary flow or use of antibiotics and antimicrobial drugs within 30 days prior to the first study visit. Patients with periodontitis were excluded from the study.

On a given day each volunteer was subjected to an examination including measurements of GI and PI at Screening (Scr), baseline (B), 3 & 6 weeks. In addition, unstimulated saliva samples were obtained by spitting method at B, 3 & 6 weeks and immediately frozen at −20° C. until further processing. The samples were then thawed, centrifuged at 2600 g for 15 minutes at 4° C., and stored at −80° C. until analysis.

Laboratory Stage

For the initial validation phase, the direct saliva transcriptome analysis (DSTA) was performed that uses cell-free saliva supernatant instead of isolated mRNA for saliva transcriptomic detection (Lee et al., 2011). In this study, 10 salivary exRNA biomarker candidates for gingivitis, discovered using the Affymetrix microarray HTA 2.0, were evaluated by reverse transcription quantitative real-time PCR (RT-qPCR) in 30 gingivitis samples from the clinical phase at B, 3 & 6 weeks. The qPCR associated with melting-curve analysis was conducted by the use of the LightCycler® 480 Real-Time PCR System by Roche Applied Science with a fixed thermal-cycling program. All primers used in RT-qPCR were designed by use of PRIMER3 software, and produced by Sigma after a BLAST search.

Statistical Analysis

Kruskal-Wallis tests were used to compare quantitative markers and chi-squared test to compare categorical markers between the two groups (healthy and gingivitis) in the discovery phase of transcriptomic analysis. Statistical comparison by the analysis of variance (ANOVA) was performed at a significance level of $p<0.05$. In addition, the association between exRNA biomarker changes and initial microarray data was investigated. Afterwards, the linear regression analysis was used to construct the final panel of biomarkers with best clinical performance for gingivitis detection. A paired t-test along with the 95% confidence interval (CI) was used to compare GI and PI scores over different time periods. In addition, a generalized estimating equation (GEE) models were added to show the overall trends across all 3 time points (B-week 3-week 6). Finally, intra- and interindividual variability between two different clinical investigators was examined using the kappa statistic (McHugh et al., 2012, Biochem. Med. (Zagreb), 22, 276-282).

The results of the experiments are now described.

HTA Microarray Profiling

The discovery phase using Affymetrix HTA microarray profiling on 50 gingivitis and 50 healthy individuals revealed 25 salivary exRNA biomarker candidates that were differentially expressed between gingivitis and healthy subjects ($p<0.05$): 4 with increased expression and 21 with decreased expression [1.4-2.9 absolute fold change] (FIG. 1). The top 10 salivary exRNA biomarker genes were advanced for the validation phase, including 3 lnc RNAs [NONHSAT006501.2, NONHSAT071649, NONHSAT005224] and 7 mRNAs [AF156166, AJ420500, NR_003225, NM_001146157, AL832615, NM_003064, NM_019060].

Validation of 10 Salivary exRNA Biomarker Candidates for Gingivitis by qRT-PCR.

FIG. 2 presents the direction of the slopes of the marker from the generalized estimating equation (GEE) models. Eight out of 10 exRNA biomarkers were significantly increased [NONHSAT071649 (m2), NONHSAT005224 (m3), AF156166 (m5), AJ420500 (m6)] or decreased [NONHSAT006501.2 (m1), NR_003225 (m4), NM_001146157 (m7), NM 019060 (m10)] over time ($p<0.001$). Each of the validated exRNA target is concordant with the HTA 2.0 microarray data (FIG. 2).

qRT-PCR results showed similar trends as revealed by the HTA 2.0 Affymetrix array analysis, i.e. NONHSAT006501.2 (m1) showed an average decrease of 5.59 fold ($p<0.001$), while NONHSAT071649 (m2) revealed an average increase of 5.54 fold ($p<0.001$) (FIG. 3). In addition, FIG. 3 presents a plot with fold changes and 95% confidence intervals (CIs) for each marker on the log base 2 scale for B, 3 and 6 weeks time point.

Linear Regression Analysis

Figure 4:
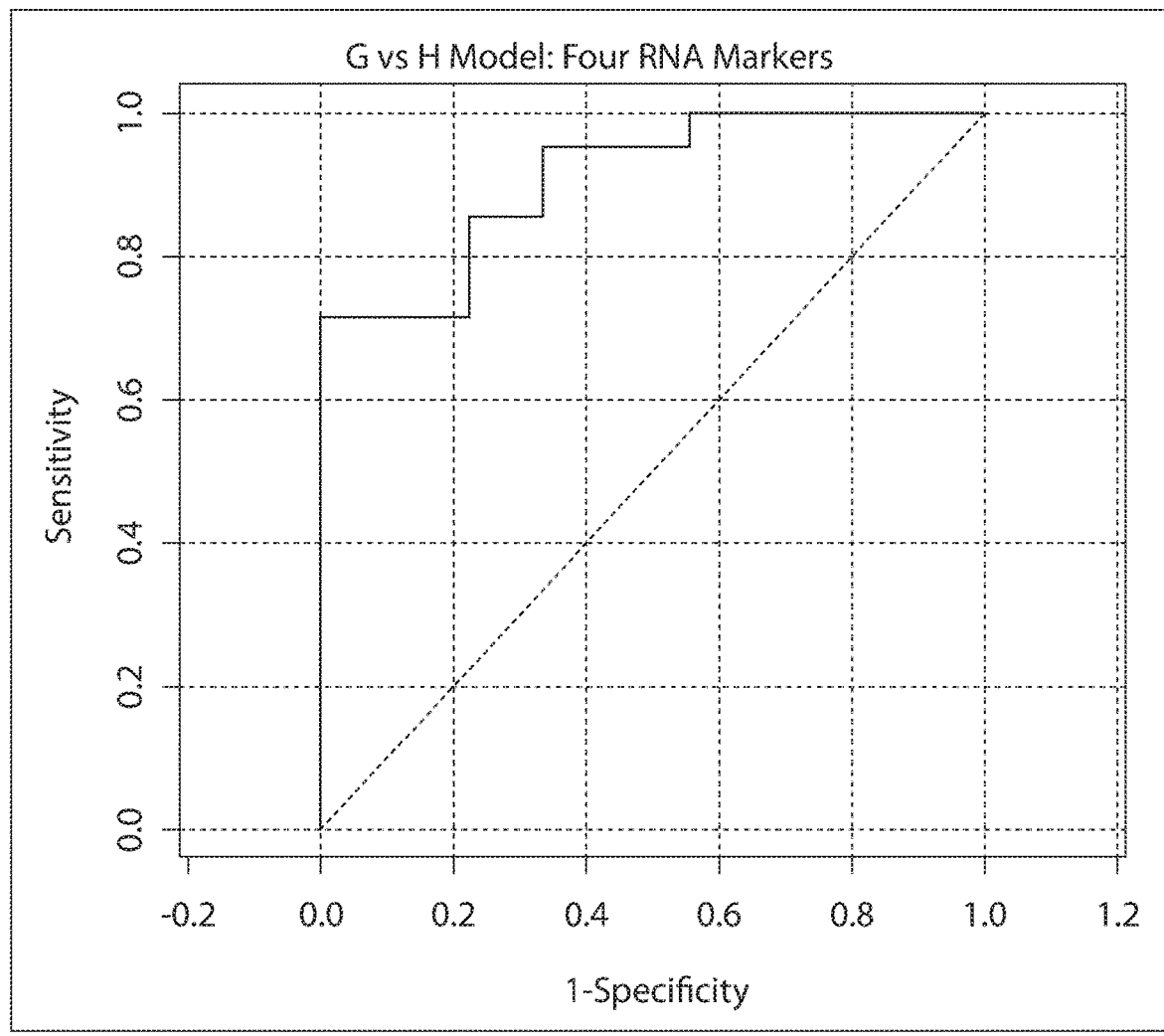
FIG. 4 depicts the results of example experiments demonstrating the performance of salivary exRNA biomarkers to classify gingivitis from healthy subjects with no periodontal disease [baseline to 6 weeks], [4 exRNAs: NONHSAT006501.2 (m1); NONHSAT071649 (m2), NM_001146157 (m7), NM_019060 (m10)] [0.91 AUC, 71% sensitivity, 100% specificity].

The potential clinical discriminatory power of the developed salivary exRNA for gingivitis detection was evaluated. Linear regression analysis of 8 validated exRNAs revealed that four exRNA marker model [NONHSAT006501.2 (m1), NONHSAT071649 (m2), NM_001146157 (m7), NM_019060 (m10)] could potentially provide a discriminatory performance of 0.91 AUC (area under the curve) with 71% sensitivity and 100% specificity (FIG. 4).

Clinical Outcomes

Figure 6:
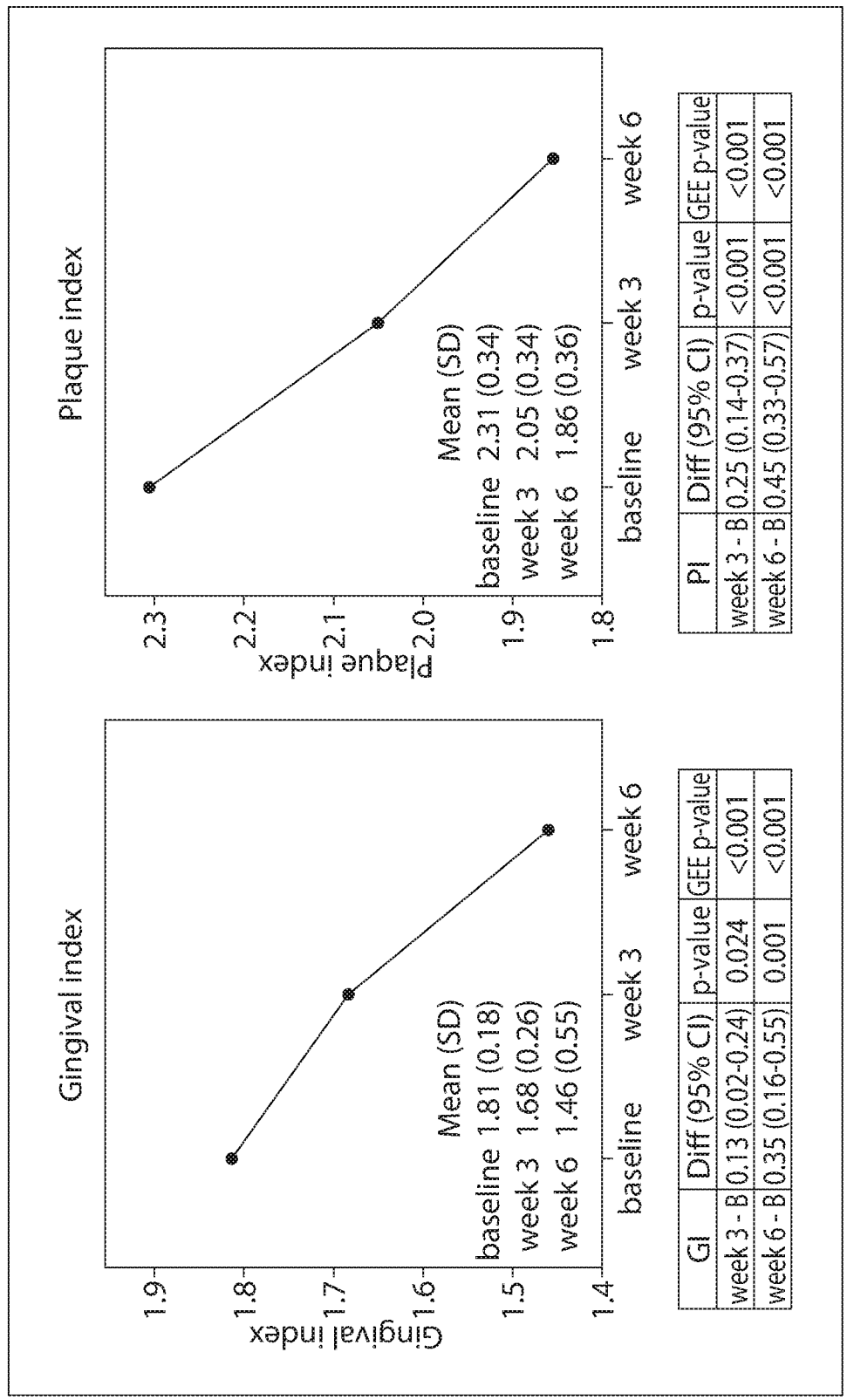
FIG. 6 depicts the results of example experiments demonstrating a comparison of the Gingival Index and the Plaque Index scores over time.

FIG. 5 presents the clinical and demographic data collected for the 30 subjects (mean age 28.2±7.77, F=17; M=13M), involved in the validation phase (i.e. subject's age, gender, GI and PI scores at baseline, after 3 and 6 weeks). Both GI and PI(FIG. 6) showed significantly decreased scores over time [i.e. GI for B-week 6 (0.001) and PI for B-week 6 (<0.001)] due to good oral hygiene regimens implemented by brushing with toothpastes. The GI scores improved for 60% and PI for 93.3% of subjects over the period of 6 weeks.

Figure 7:
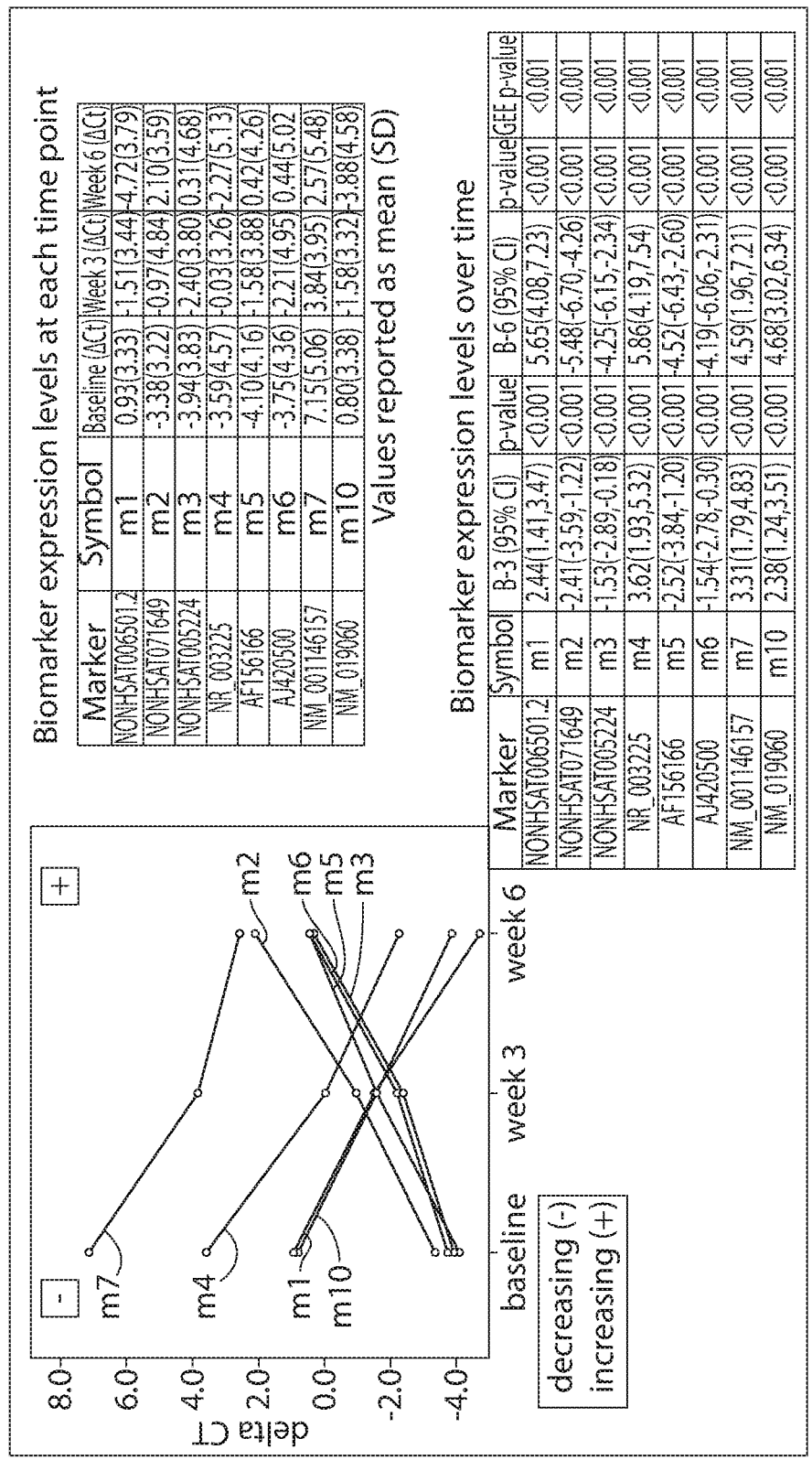
FIG. 7 depicts the results of example experiments demonstrating a comparison of biomarker expression levels of 8 validated salivary exRNAs at each time point and longitudinally (normalized ΔCt values according to reference gene ACTB). P-values are represented for each marker over time [Baseline-week 3 (B-3) & Baseline-week 6 (B-6)]. The graph presents statistically significant overall trends, increasing or decreasing, for each marker across all 3 time points (baseline, week 3 & week 6).

Assessment of Biomarker Expression Levels Between Groups at Each Time Point and Longitudinally The levels of 8 salivary exRNA biomarkers were measured at each time point and longitudinally (FIG. 7). All 8 validated exRNA biomarkers were statistically significantly different over time (B-week 3 & B-week 6) (GEE p-values<0.001) showing either increased [NONHSAT071649 (m2), NONHSAT005224 (m3), AF156166 (m5), AJ420500 (m6)] or decreased trend over time [NONHSAT006501.2 (m1), NR_003225 (m4), NM_001146157 (m7), NM_019060 (m10)] (FIG. 7).

Investigation of Potential Clinical Evaluators Bias

Figure 8:
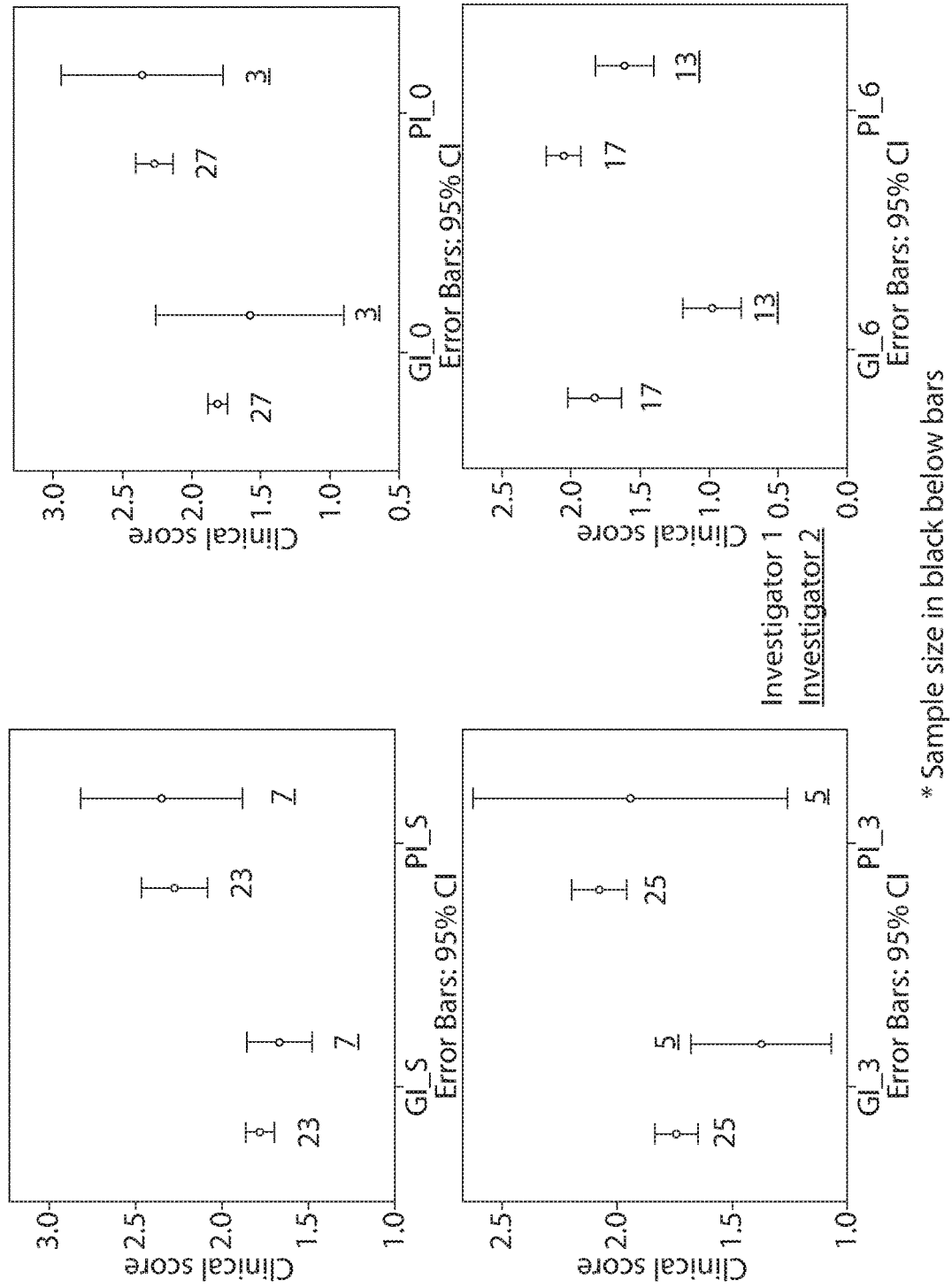
FIG. 8 depicts the results of example experiments of a clinical evaluator investigation over time (at screening, baseline, 3 and 6 weeks).

The were no significant inter-examiner differences between the clinical evaluators, except for time point 6 weeks (FIG. 8). This is despite the fact that all examiners were initially calibrated.

Differentially Expressed Salivary exRNA Analysis

The HTA array profiling revealed initially 25 salivary exRNA biomarker candidates that were differentially expressed between gingivitis and non-gingivitis healthy subjects (p<0.05) (FIG. 1). Of these, ten were selected as candidate biomarkers for further validation in the clinical study based on their known association with inflammation and periodontal diseases as well as p-values (p<0.05) and the highest absolute fold changes in their expression levels between gingivitis and control groups with healthy periodontium. Interestingly, only very few had been previously reported in bodily fluids, but not in human saliva.

Eight out of 10 selected salivary exRNAs, initially validated in the clinical study [3 lnc exRNAs: NONH-SAT006501.2 (m1), NONHSAT071649 (m2), NONH-SAT005224 (m3) as well as 5 mRNAs: NR_003225 (m4), AF156166 (m5), AJ420500 (m6), NM_001146157 (m7), NM_019060 (m10)], showed statistically significant differentially expressed levels (p<0.05) over time (Baseline-week 3 & Baseline-6 week) in the same directions as the HTA microarray discovery data (FIG. 2). Thus, qRT-PCR analysis further supported microarray discovery findings, however with increase in their alteration levels compared to the initial data. This change might be a result of the interindividual variability in exRNA patterns.

Biomarker Panel for Gingivitis

The linear regression analysis of the top ranking, initially validated, salivary exRNA markers revealed that a four exRNA marker model [NONHSAT006501.2 (m1), NONH-SAT071649 (m2), NM_001146157 (m7), NM_019060 (m10)] could potentially provide a discriminatory performance of 0.91 AUC with 71% sensitivity and 100% specificity (FIG. 3).

Description of Potential Functions of Initially Validated exRNAs for Gingivitis

Long noncoding RNAs (lncRNAs) have generated widespread interest in recent years as potentially associated in the induction of particular diseases or developmental processes, but knowledge of the particular pathogenetic mechanisms of actions is still limited. An area of studying lncRNAs, their biology and functions, is still emerging (Kung et al., 2013, Genetics, 193, 651-669).

NONHSAT006501.2 (m1) [Gene & mRNA Accession: 573288, Gene Symbol: SPRR1A, Noncode Gene ID: NONHSAG002962.2, lnc-SPRR1A-1-1_dup1,lnc-S] is reported as related to epidermatitis development, keratinocyte differentiation and keratinization (Gibbs et al., 1993, Genomics, 16, 630-7; Stemmler et al., 2009, Int. J. Immunogenet., 36, 217-22);

NONHSAT071649 (m2) [Gene Accession: OTTHUMT00000328143, Gene symbol: AC073046.25, lnc-TET3-2:1] is a member of the ten-eleven translocation (TET) gene family, that plays a role in the DNA methylation process (Langemeijer et al., 2009, Cell Cycle, 8, 4044-8);

NONHSAT005224 (m3) [Gene Accession: OTTHUMT00000033693, Gene symbol: RP5-965F6.2] is a new lncRNA and has not been reported yet in the publications.

Messenger RNAs (mRNAs) are an emerging target for noninvasive diagnostic applications. The identification of saliva-derived mRNA in normal and cancer patients (Li et al., 2004, J Dent Res, 83, 199-203; Hu et al., 2008, Clin. Chem., 54, 824-832) and other forensic applications (Juusola et al., 2005, Forensic Sci. Int., 152, 1-12) have opened up a new avenue for further clinical usage.

NR_003225 (m4) [Gene Accesion: NR_003225, Gene symbol: LGALS3] is a non-coding RNA, that encodes a member of the galectin family of carbohydrate binding proteins that play a role in apoptosis, innate immunity, neutrophil, eosinophil & macrophage chemotaxis and negative regulation of endocytosis. It exhibits antimicrobial activity against bacteria and fungi (Raz et al., 1991, Cancer Res., 51, 2173-8). It is also associated with increased risk for rheumatoid arthritis (Atabaki et al., 2017, Biomed Rep. 6, 251-255). Therefore, in gingivitis, which is an inflammatory conditions of the gingival tissues, decreased levels of NR_003225 was observed, both in the initial microarray data and in qRT-PCR results.

AF156166 (m5) [Gene Accession: AF 156166] is *Homo sapiens* putative tumor suppressor mRNA. However, not much information about this specific exRNA can be found in the literature (Boultwood et al., 2000, Genomics 66, 26-34).

AJ420500 (m6) [Gene Accession: AJ420500, Gene symbol: SOX4] functions in the apoptosis pathway leading to cell death as well as to tumorigenesis, and may mediate downstream effects of parathyroid hormone (PTH) and PTH-related protein (PTHrP) in bone development. It is also related to obesity and type 2 diabetes (Ragvin et al., 2010, Proc Natl Acad Sci USA, 107, 775-80).

NM_001146157 (m7) [Gene Accession: NM_001146157, XM_001723781, XM_002343005, XM_926530, XM_937048, Gene symbol: FAM25A] when it is downregulated, it represents an increased risk for inflammation and infectious disease with a decrease in immune response (Wang et al., 2014, PLoS One, 9, e92504; Mauritz et al., 2010, J Biomed Opt., 15, 030517; Deloukas et al., 2004, Nature, 429, 375-81).

NM_019060 (m10) [Gene Accession: NM_019060, Gene symbol: CRCT1]. This mRNA has been recently linked to esophageal cancer (Wu et al., 2016, Tumour Biol., 37, 8271-9) and oropharyngeal squamous cell carcinomas (Masterson et al., 2015, Cancer Sci., 106, 1568-75). However, the underlying mechanism remains still unclear. It promotes tumor cell apoptosis and upregulates the expression of apoptosis-related proteins (Wu et al., 2016, Tumour Biol., 37, 8271-9).

The above-mentioned unique salivary exRNAs can be very useful in discrimination of patients with gingivitis and with healthy periodontium as well as in monitoring regression of gingivitis. The use of saliva transcriptomes can be further advanced for translational and clinical applications.

These experiments demonstrate that 8 out of 10 examined salivary exRNA biomarkers for gingivitis were significantly increased or decreased over time (baseline to week 3 & baseline to week 6) in the same directions as based on the independent discovery sample with a different technological microarray platform. The four exRNA marker model [NONHSAT006501.2, NONHSAT071649, NM_001146157, NM_019060] could potentially provide a discriminatory performance of 0.91 AUC with 71% sensitivity and 100% specificity. Based on clinical outcomes (decrease in GI & PI), improving over time during these 6 weeks with good oral hygiene regimen (i.e. brushing with toothpastes), this study provides good evidence that 8 validated salivary exRNA markers may be useful in reflecting oral health and can be used to monitor disease regression over time.

The disclosures of each and every patent, patent application, and publication cited herein are hereby incorporated herein by reference in their entirety. In the event of a conflict in a definition in the present disclosure and that of a cited reference, the present disclosure controls. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treating gingivitis in a subject in need thereof, comprising:
   a. obtaining a saliva sample of the subject;
   b. detecting the level of the biomarker NONHSAT006501.2 in the saliva sample of the subject, and optionally at least one biomarker selected from the group consisting of NONHSAT071649, NONHSAT005224, LGALS3, AF156166, SOX4, FAM25A, AL832615, SLPI, and CRCT1;
      wherein the subject is identified as being in need of treatment when the level of the at least one biomarker in the saliva sample of subject is differentially expressed when compared with the level of the biomarker in the comparator control, thereby diagnosing gingivitis in the subject; and
   c. treating the subject for gingivitis, consequent to the detection in step b; wherein said treating comprises one or more of dental procedures, periodontal procedures, surgical procedures, administration of pharmaceuticals, therapeutics or prophylactics; professional dental cleaning; scaling and root planning; dental restoration, use of chlorohexidine rinses; oral irrigation, interdental brushing, use of toothpastes containing Stannous, Zinc, Triclosan, and/or hydrogen peroxide; use of mouthwashes containing Triclosan, Cetylpyridinium chloride, other quaternary ammonium chlorides and/or essential oils.

2. The method of claim 1, wherein the level of the at least one biomarker in the saliva sample is determined by measuring the level of mRNA of the at least one biomarker in the saliva sample.

3. The method of claim 1, comprising detecting that the level of at least one biomarker selected from the group consisting of NONHSAT071649, NONHSAT005224, AF156166, and SOX4 is increased as compared to the level of the at least one biomarker in the comparator control.

4. The method of claim 1, comprising detecting that the level of at least one of said biomarkers is decreased as compared to the level of the at least one biomarker in the comparator control.

5. The method of claim 1, wherein the comparator control is the level of the at least one biomarker in the saliva sample of a subject or population not having gingivitis.

6. The method of claim 5, wherein the comparator control is at least one selected from the group consisting of a positive control, a negative control, a historical control, a historical norm, or the level of a reference molecule in the biological sample.

7. The method of claim 5, wherein the subject is a mammal.

8. The method of claim 5, wherein the subject has started treatment for gingivitis; further comprising the steps of:
   d. detecting that the level of the at least one biomarker in the saliva sample of the subject is differentially expressed as compared to the level of the at least one biomarker in a comparator control, and
   e. detecting that the subject is responsive to the treatment when the level of the at least one biomarker in the saliva sample of subject is differentially expressed when compared with the level of the biomarker of the comparator control.

9. The method of claim 8, wherein the comparator control comprises a saliva sample of the subject obtained prior to initiation of the treatment.

10. The method of claim 8, wherein the comparator control comprises a saliva sample of the subject obtained at an earlier time point during the treatment.

* * * * *

SEQUENCE LISTING

<160> NUMBER OF SEQ ID NOS: 10

<210> SEQ ID NO 1
<211> LENGTH: 317
<212> TYPE: DNA
<213> ORGANISM: Artificial Sequence
<220> FEATURE:
<223> OTHER INFORMATION: Synthetic

<400> SEQUENCE: 1
gtaatgtggt ccacagccat gcccttgagg agctggccac tggatactga acaccctact    60
ccattctgct tatgaatccc atttgcctat tgaccctgca gttagcatgc tgtcaccctg   120
aatcataatc gctcctttgc acctctaaaa agatgtccct taccctcatt ctggagggct   180
cctgagcctc tgcgtaaggc tgaacgtctc actgactgag ctagtcttct tgttgctcgg   240
gtgcatttga ggatggattt ggggaaggat caagtgaacc atccctagtc ttccttcaat   300
aaataacttt taactcc                                                  317

<210> SEQ ID NO 2
<211> LENGTH: 390
<212> TYPE: DNA
<213> ORGANISM: Artificial Sequence
<220> FEATURE:
<223> OTHER INFORMATION: Synthetic

<400> SEQUENCE: 2
cgctccgccc cggaggcggc gggcaggcag cactgccttc tccagcgtcc agaccctgga    60
ggaaaaatac caggagaaac tgctcactca gctctgcccc caccacaccc ctacctgctc   120
aactcatgcc tgggtccagg gtgggtgagg gtgaagaacc caccgggcca agatgatccc   180
ttttctgagg gctgctgctg gtgtcctccc ccagatcctg ggcccagca ggtgggagag    240 tggcccccta cggagtccga tcagactgct gcagaggagg tgaagagggg ttgagaagag   300
gcatccatcc acgagactga agccacttgc cttcacccct gtagactctt gactgttcta   360
ggcgagaagg acctgttggt ggcctttgga                                    390

<210> SEQ ID NO 3
<211> LENGTH: 547
<212> TYPE: DNA
<213> ORGANISM: Artificial Sequence
<220> FEATURE:
<223> OTHER INFORMATION: Synthetic

<400> SEQUENCE: 3
tttctcagcc tggagactga aagctctctt tggctgttgg ccctcccagg cagagtccac    60
tggctgttag ggtgaaatgg ggctgatgct tcctggaatc caccagaagt atgcaaattg   120
caccatctct ttcagctgcc tgcgcctgca ttccatcgag gattccggct cgtccccag    180 tggcaacaac tagagaggag gtgaggatcc ccggcgctgc catctgatag gctgtctccc   240

| | |
|---|---|
| tagctcctct tgcactggca atcctttcat cacacaggcc ttgttttgaa gggacctatt | 300 |
| ccacccacag tcgtttctca cctctaggag gccaaaaagc tgtagtcatt gctgtggtat | 360 |
| caggaactcg agttcctctc agaggtgttg tgaagagctt cccttccaac agtacatggc | 420 |
| ctaaatacca gggaggaagt ttctgacttt ttccatcttc agtaaaacag aacctctgtt | 480 |
| gtggatgcag tggctttgca aggagagtgg cattgtctct tggtgaatgt agttgttcaa | 540 |
| gtcatgg | 547 |

```
<210> SEQ ID NO 4
<211> LENGTH: 1973
<212> TYPE: DNA
<213> ORGANISM: Artificial Sequence
<220> FEATURE:
<223> OTHER INFORMATION: Synthetic

<400> SEQUENCE: 4
```

| | |
|---|---|
| gtgtgcaaat agaggaataa atagcagggc agcaactatg tctggaggtc attgtctttc | 60 |
| ctgtctcagt agtaatcaat cactgcttat cttcaaaaac ccagagtagg ggatggggca | 120 |
| gttagtgggg acagagggca gatgggtaag attcagagca caggctagtg tgacggaagt | 180 |
| ttaaacttgt gagttaaata gggtttggca atctagctgg atagcatccc tgcccccttga | 240 |
| agagatgttt ttgtggcgcc acactactga cttaggcata atgcctagag atggattaga | 300 |
| actgcacaat gaactagtgg tgaggttcag tttaatggaa attggtgaaa gcttttagga | 360 |
| taaaatgata atctttgttt ctttcaggaa aatggcagac aattttttcgg taagtgtttt | 420 |
| atgcctgttt cttccccttg atcagctcca catggttgag ggttgggggt tttgttttta | 480 |
| ccatgacttt ccctttttcac tctcccactg cgtggcttcc cctggactca tttgtccaat | 540 |
| gagggcttgc aagctggagc cttgttttc cagcagcaga tttgggaaga aagccaggca | 600 |
| gagcgaggcc tgggactcac tcacagtaac cctttcacca aaaggcccag ggcggaaggg | 660 |
| agtggactct gccggcagga gctgagaaat cctctgagta gcgggaagtg cggtacagtc | 720 |
| tgggcattct gatgtttgtg attgtttttc tcacggtgat gaaaagtat gtgctataag | 780 |
| tagaggagcg ctaactcctg acttgagcta attatgaaaa tgcagccctc cctgatctga | 840 |
| gacgttggga ggcaagaata aagtgaaaaa gtatatgtaa tcccaacatc taatttttagt | 900 |
| cttagaaact caaactatta ataagtggaa aaagtttaat gatatgcatg taatgccttt | 960 |
| gccatattcc tctccttctt agatcacata ttcctatttt cctgaaaatt ctgcttttga | 1020 |
| gaatgctttc tgtcccgtaa ttgtgtatgt cttttctttcc agctccatga tgcgttatct | 1080 |
| gggtctggaa acccaaaccc tcaaggatgg cctggcgcat gggggaacca gcctgctggg | 1140 |
| gcagggggct acccagggc ttcctatcct ggggcctacc ccgggcaggc accccaggg | 1200 |
| gcttatcctg gacaggcacc tccaggcgcc taccctggag cacctggagc ttatcccgga | 1260 |
| gcacctgcac ctggagtcta cccagggcca cccagcggcc ctggggccta cccatcttct | 1320 |
| ggacagccaa gtgccaccgg agcctaccct gccactggcc cctatggcgc cctgctggg | 1380 |
| ccactgattg tgccttataa cctgcctttg cctgggggag tggtgcctcg catgctgata | 1440 |
| acaattctgg gcacggtgaa gcccaatgca aacagaattg ctttagattt ccaaagaggg | 1500 |
| aatgatgttg ccttccactt taacccacgc ttcaatgaga caacaggag agtcattgtt | 1560 |
| tgcaatacaa agctggataa taactgggga agggaagaaa gacagtcggt tttcccattt | 1620 |
| gaaagtggga aaccattcaa aatacaagta ctggttgaac ctgaccactt caaggttgca | 1680 |
| gtgaatgatg ctcacttgtt gcagtacaat catcgggtta aaaaactcaa tgaaatcagc | 1740 |

```
aaactgggaa tttctggtga catagacctc accagtgctt catataccat gatataatct    1800
gaaaggggca gattaaaaaa aaaaaaagaa tctaaacctt acatgtgtaa aggtttcatg    1860
ttcactgtga gtgaaaattt ttacattcat caatatccct cttgtaagtc atctacttaa    1920
taaatattac agtgaattac ctgtctcaat atgtcaaaaa aaaaaaaaaa aaa           1973
```

<210> SEQ ID NO 5
<211> LENGTH: 722
<212> TYPE: DNA
<213> ORGANISM: Artificial Sequence
<220> FEATURE:
<223> OTHER INFORMATION: Synthetic

<400> SEQUENCE: 5

```
gagactgcat agggctcggc gtggatcttg ttaatgctga ttctggtaca gtaggtctag     60
ggcggggcct gagattctgc atttctaaca agaacccagg tgatgctgac gctgctgggc    120
caaaaaagac actttgagta gcaagggtta ggcaaccttt aaagggccct tcaagagtct    180
aagattccat gaaggatact atttcctcta caagcttgtg aaagtcttcc agtgctactg    240
ggaatggggt acaggataaa atctcactgt tttgacctca cagaagtaaa cccctagaat    300
catgttctca aaatgaaaca ctggattgct gaactgatgg cattgagaat taaggctcca    360
aaatcctggg agtttcatac ctaactccac tgcctttgcc ttatgatgca cactgctccc    420
tctatccctc cctcccaggg tctgcagaga tgaactatgc tgttttaggt ctcattggtc    480
cttatacctt ccctaaacca ggaggacttt ggagcctgct gacacaggga gttctacatg    540
tctaagcacg cagctgctag agtcctcagc catctgagct aaatagctgc tcagagacaa    600
ttagtacacc tccgtatytt acagataaag gaactgaagt ccaaacaagc caagctaccc    660
aaccaaggct cacagcaggc aagaggataa aaaccatgtc ctttgactcc caggttagtt    720
tt                                                                   722
```

<210> SEQ ID NO 6
<211> LENGTH: 1233
<212> TYPE: DNA
<213> ORGANISM: Artificial Sequence
<220> FEATURE:
<223> OTHER INFORMATION: Synthetic

<400> SEQUENCE: 6

```
ccacgcgtcc gcatattttt tcttttgtcc ctttttttct ttcctttctt tttacttcct     60
ttatttcttt attccttcct tttccttttt ttcttttttt tttcttttt ttttttttt      120 ggtagttgtt gttacccacg ccattttacg tctccttcac tgaagggcta gagttttaac    180
ttttaatttt ttatatttaa atgtagactt ttgacactt taaaaacaa aaaaagacaa      240 gagagatgaa aacgtttgat tattttctca gtgtatttt gtaaaaaata tataaagggg     300
gtgttaatcg gtgtaaatcg ctgtttggat ttcctgattt tataacaggg cggctggtta    360
atatctcaca cagtttaaaa aatcagcccc taatttctcc atgtttacac ttcaatctgc    420
aggcttctta aagtgacagt atcccttaac ctgccaccag tgtccaccct ccggccccg     480 tcttgtaaaa aggggaggag aattagccaa acactgtaag cttttaagaa aaacaaagtt    540
ttaaacgaaa tactgctctg tccagaggct ttaaaactgg tgcaattaca gcaaaagggg    600
attctgtagc tttaacttgt aaaccacatc ttttttgcac ttttttttata agcaaaaacg    660 tgccgtttaa accactggat ctatctaaat gccgatttga gttcgcgaca ctatgtactg    720
```

| | |
|---|---|
| cgttttcat tcttgtattt gactattaa tcctttctac ttgtcgctaa atataattgt | 780 |
| tttagtctta tggcatgatg atagcatatg tgttcaggtt tatagctgtt gtgtttaaaa | 840 |
| attgaaaaaa gtggaaaaca tctttgtaca tttaagtctg tattataata agcaaaaga | 900 |
| ttgtgtgtat gtatgtttaa tataacatga caggcactag gacgtctgcc ttttaaggc | 960 |
| agttccgtta agggttttg ttttaaact tttttttgcc atccatcctg tgcaatatgc | 1020 |
| cgtgtagaat atttgtctta aaattcaagg ccacaaaaac aatgtttggg ggaaaaaaaa | 1080 |
| gaaaaatca tgccagctaa tcatgtcaag ttcactgcct gtcagattgt tgatatatac | 1140 |
| cttctgtaaa taactttttt tgagaaggaa ataaaatcag ctggaactga accctaaaaa | 1200 |
| aaaaaaaaaa aaaaaaaaaa aaaaaaaaaa agg | 1233 |

<210> SEQ ID NO 7
<211> LENGTH: 362
<212> TYPE: DNA
<213> ORGANISM: Artificial Sequence
<220> FEATURE:
<223> OTHER INFORMATION: Synthetic

<400> SEQUENCE: 7

| | |
|---|---|
| tcagcatcct agttcaccac tgtctgctgc cacacgatgc tgggaggcct ggggaagctg | 60 |
| gctgccgaag gcctggccca ccgcaccgag aaggccaccg agggagccat tcatgccgtg | 120 |
| gaagaagtgg tgaaggaggt ggtgggacac gccaaggaga ctggagagaa agccattgct | 180 |
| gaagccataa agaaagccca agagtcaggg gacaaaaaga tgaaggaaat cactgagaca | 240 |
| gtgaccaaca cagtcacaaa tgccatcacc catgcagcag agagtctgga caaacttgga | 300 |
| cagtgagtgc acctgctacc acggcccttc cccagtctca ataaaaagcc atgacatgtg | 360 |
| ta | 362 |

<210> SEQ ID NO 8
<211> LENGTH: 4471
<212> TYPE: DNA
<213> ORGANISM: Artificial Sequence
<220> FEATURE:
<223> OTHER INFORMATION: Synthetic

<400> SEQUENCE: 8

| | |
|---|---|
| gtggctcttg agcatgggtg ggggaagccc ccacatatct gagtcagtgc cacctggaca | 60 |
| ctacccttgg agcatcctgc tgaggtggcc attcaggttt ctttcctttt cctttattc | 120 |
| cactgtttgc ctcggacatg aaacatctca cagactgcct ggaagaaggt ggagcagact | 180 |
| ggggttaatg gtcagcagca gcagcatccc caccactggg gctatccctt tttaggccct | 240 |
| taccatgggc caaacactga gccgtgtgct tcgtgtaact tctaagcacg cttacctgat | 300 |
| agagtgccag caaagactca agaggtgcc tgggcttggc acatagtagc tattgctact | 360 |
| attatgaatg ttgttttgtc tttgtttttg ttttgagaca gggcctcact ctgttgccca | 420 |
| ggttggagta cagcagtgcc atcatggctc actgaggcct caacctccct gggtttgggc | 480 |
| agtcctcccg cctcggcctc ccgagtggct gggactacag gtgtgcgcca ccaagcccgg | 540 |
| ccggtttttt gtattttcag tagagactgg ttttgccaag tcgcccaggc tggtttcgaa | 600 |
| ctctgtgatc ccagcacttt ggaggccga ggcgggtgga tcatgaggtc aggagatcga | 660 |
| gaccatcctg gctaacaagg tgaagccccg tctctactga aaatacaaaa aattggccgg | 720 |
| gcgcggtggc gggcgcctgt ggtcccagct gctcgggagg ctgaggcggg agaatggcgt | 780 |
| gaacccggga agcggagctt gcagtgagcc gagattgcgc cactgcggtc cgcagtccag | 840 |

```
cctgggcgac agagcgagac tctgtctcaa aaaaaaaaaa aaaaaaaaaa aatgccaagc    900
tcacccagaa ataaccccgt gcatatatgg tcaacagatc tttgacaagg ccatcaagga    960
tatacaatgt agattctttt attcctttac tttcttaata gacttgcttt cactgtactg   1020
taaaaaaaaa aaaggcacaa tgtagaaagg aaactctctt caatgaatgg tgttggggaa   1080
agtgcatgaa aaagaatgaa attgcacact tgttttacat catatacaga aaattagctc   1140
aaagtggatt aaagatttaa atgtaatatc tgaaccatgt aaatcctgg aagtaaacat    1200
agggaaaaat ctcctcgaca ttggtcataa ttggcaatat ttttttgat gtaacaccaa    1260
agcacaggca acaaaagtga aataaataa atgggactac atcaatctta aaaggttta    1320
cacagcaaag gaaccatga caaaatgaaa aggcaaccta cgggatggaa gaaaatattt    1380
gcgacccata tatttgataa ggggttattt gaaaaaatat aaggaattca cacaattcaa   1440
tagcaaaaat aataaaatac atgaataacg caattaaaaa taggcaaagg accccaatgg   1500
acttttttcc ccaaggaaga tatacaaatg gccagccagc atatgaaaag gtgctcaaca   1560
ccactaatca tcagagaaat gcaaatcaaa accacagtga gatattgcct cataggggtag  1620
gatggctctt ataaaaaaac gacaagagat aacaagtgtt ggcgaaagca tagaggaaag   1680
agaaccttg tacactgttg gttggaatgt aaagtggtat aaccttttaca gaaaacagta   1740
tggaggttcc tcaaaaaatt agaagcagaa ctaccatacg attcagcaat caggttagaa   1800
ccttgaagag agatctgcgc ccatgtttta ttacaacact attcacaata cccaagatat   1860
ggaaacagcc taagtgtcca gcaacagatg aatggataaa taaatacat ataaacaatg    1920
gactattagc cattcaaaag aagaaactcc tgtcctggat aaacctggag gacattacgc   1980
taagtgaaat aagccagaca ccgaaagaca agttttgtat gatctcactt atatgtggga   2040
tctaagagag tcaaactcat aaaaacagat agtagaatgg tggttgccaa gggctggagg   2100
tgggaaaat gggaagctat taatcaaagg gtgtaaactt tcagttataa gatgaacaaa    2160
ttctggagat ttaatgtaca gcataggtgg taatggatgt aataaatttg attgtgataa   2220
ttagtacaca atatatacat atatgaaatc atcacattgt atgcattaaa tatacacaat   2280
ccttgtcaac tcaatatttt taaaaaaatg tttaaaatgc ctaggtcata agaattctga   2340
gaatgaaata caacaacata catgaatgga cctgctacac agaaggtgct aaataggttt   2400
gttttgtttt attttatttc aactctggca gatgtagacc tattgggaaa gaatatagaa   2460
tgcacttgtg cacaaggatt atctatacga tggttaaata tcctgcatac atgccatgtc   2520
atttctactc ctcagtcaat ggataataaa agcagaacca gccttctggt ggtcacaaaa   2580
cattttgaca tgagaaaggc tgatcatgag caatctggca atgtacatcc cagagcgtgc   2640
atgccctttg acccacagct accatgatgt catgtctagc aattagtcct aaggagatga   2700
tcagagatgt gtaaagagat ttcattctaa cagcatcctc tgtagtggta tatgtcaggg   2760
gctggtaagc catgtccaga ggagcaggct gcatctggtc caccacctgt ttttgtaaag   2820
tttatcagaa cacagtcatg cccattcatt tacaaattgt gtatggcttc tttccctgca   2880
acagcagagt tgagtgttgc aacagaaacc tatggcctgc agagtttaaa atatctaccc   2940
tttggccttt tataaaaaaa gtttactgat tcctggtgag tatattaaaa agttaggaaa   3000
acctaaatct tccagagtgg agaattagaa agtaagacgt gttgtatata agacagacag   3060
tttgtgtgtg cgtttatttta taaatatatt atttttgaaat aatgttgtcg acatatgttg  3120
caggtcttaa aaattggtca atatatagtg ttaatcaaaa aatggcaaat tgtaaaatgt   3180
```

| | |
|---|---|
| agacagaatg tgattgtgta ttttgtgcat acaccaacag aaaagggtgc taggaaacct | 3240 |
| gtggaccaac atactaagtg tggctctttt gatggtggta tcatggattt ttaaaaatct | 3300 |
| tcttggtttt ctgtagattc tgactttcct gtaatgagta tgaataagta tgtatttctt | 3360 |
| gagaaatgag aaaataactt tatcttccca gatttctcat aattgaaaat gttggaataa | 3420 |
| atggtcctgg gacagatctt tccattgaga agggcggaag ggaaccctg gggattcagc | 3480 |
| tgggtttctg ttgcatttct ggtaacacac agttgtgaaa agccagtgtt ggccattccc | 3540 |
| caggacagtc tggggtagag gaggtcagga tttaactact tgagggtccg gggaacagat | 3600 |
| gtggccacag tccttcctga ctcactgttt tcccttccac agtccccgtc ttctcttcac | 3660 |
| tgatgcacat agatgcctga ccagaggaga gatttagttt tcgtccaagg attatctgtt | 3720 |
| atgttgcagt tctgaaattc cataacgtt taggctagaa cacaagtgat ttcattatct | 3780 |
| ccaatgtgta tggcttgata gaaatagatt ccattatgta gcaccttaaa tccagataaa | 3840 |
| acataaggaa tttctattcc atgtttgtat gatcaatgtt aataatctaa gaaaatctaa | 3900 |
| aaagaagcta cttcctctat tacagtatga aataaatatg ctgaatgatt tgtcttgggg | 3960 |
| ggtggaatgg aaaggtataa gactgaggag ggtgcctgtg gaacagtga taggaatcct | 4020 |
| ttcttaaggg ttgggtttta catacgtctt ttaaaataga tgtatcatt aataaattat | 4080 |
| ctgtgggcat catgaaaaaa gtgtataacg tacaacttta tgagcttgac agttggtgaa | 4140 |
| aacttttctg tttaaaattt tatttggccc tccccaaaag aaatgtttat ttatgagtat | 4200 |
| taggatagtt ccagcagtaa tgcctcaaaa gaaccaggag gtatagtgtt gtctaaaatg | 4260 |
| tggactcagg agccagactg cctggctgtg caactagcct tgtcacttcc tagatatgtg | 4320 |
| gcaagttaat taacttctca gtgttcttat ctgtagaatg gggataatcc taatatacat | 4380 |
| ctcagggtta tattacaaat ttgagaagtt aattttgtaa aggacttaga atgatatctg | 4440 |
| gcaaataaaa gtgttcataa aagcaaaaaa a | 4471 |

```
<210> SEQ ID NO 9
<211> LENGTH: 598
<212> TYPE: DNA
<213> ORGANISM: Artificial Sequence
<220> FEATURE:
<223> OTHER INFORMATION: Synthetic

<400> SEQUENCE: 9
```

| | |
|---|---|
| cagagtcact cctgccttca ccatgaagtc cagcggcctc ttcccctctc tggtgctgct | 60 |
| tgccctggga actctggcac cttgggctgt ggaaggctct ggaaagtcct tcaaagctgg | 120 |
| agtctgtcct cctaagaaat ctgcccagtg ccttagatac aagaaacctg agtgccagag | 180 |
| tgactggcag tgtccaggga agaagagatg ttgtcctgac acttgtggca tcaaatgcct | 240 |
| ggatcctgtt gacaccccaa acccaacaag gaggaagcct gggaagtgcc cagtgactta | 300 |
| tggccaatgt ttgatgctta accccccaa tttctgtgag atggatggcc agtgcaagcg | 360 |
| tgacttgaag tgttgcatgg gcatgtgtgg gaaatcctgc gtttccctg tgaaagcttg | 420 |
| attcctgcca tatggaggag gctctggagt cctgctctgt gtggtccagg tcctttccac | 480 |
| cctgagactt ggctccacca ctgatatcct ccttttggga aaggcttggc acacagcagg | 540 |
| cttttcaagaa gtgccagttg atcaatgaat aaataaacga gcctatttct ctttgcac | 598 |

```
<210> SEQ ID NO 10
<211> LENGTH: 699
<212> TYPE: DNA
<213> ORGANISM: Artificial Sequence
```

```
<220> FEATURE:
<223> OTHER INFORMATION: Synthetic

<400> SEQUENCE: 10
gcccattcca gttggagaac gtagtgagtc tttcagtgga gccagggtct ggtttgtcgt      60
gaggagctcc gcgatgtcct ctcaacagag cgccgtttcc gccaaaggct tttccaaggg     120
gtcgtcccag ggccccgctc cgtgtcccgc cccggcgccc accccggcgc ccgcctcctc     180
ctcctcctgc tgcggctccg gcaggggctg ctgcggcgac tcaggctgct gcggctccag     240
ctccaccagt tgctgctgct tcccaaggag acgccgccga cagcggagta gtggttgctg     300
ctgctgcggg ggcggcagcc agaggtccca gcgctccaac aaccggagct caggatgctg     360
ctccggctgc tgagaggccc gcaaccccca gcgctgcgct agagaaaccc gcccagccca     420
gagcgggccc gccccgctgc ggctcccacg cggggctggg cctcggagtt tgccccgtaa     480
agcgaattgc actttgatgt tcagaaaccc actttgttct cagccacgca aaactccctg     540
accccgatgt gatttttctc cccggggatt cgagagccat gcgtgggaca ctggacccta     600
ctgtctacac gggcttgcac acagcaggtg ctcagcaaat gtctattgat ttgattgtct     660
tttgaagatg tcataataaa gcttctacct cctgaaaaa                            699
```

UNITED STATES PATENT AND TRADEMARK OFFICE
CERTIFICATE OF CORRECTION

PATENT NO. : 11,124,833 B2
APPLICATION NO. : 16/171418
DATED : September 21, 2021
INVENTOR(S) : David T. W. Wong et al.

It is certified that error appears in the above-identified patent and that said Letters Patent is hereby corrected as shown below:

In the Claims

Column 46, Line 38, Claim 6, delete "5," and insert -- 1, --, therefor.

Column 46, Line 43, Claim 7, delete "5," and insert -- 1, --, therefor.

Column 46, Line 45, Claim 8, delete "5," and insert -- 1, --, therefor.

Signed and Sealed this
Thirtieth Day of November, 2021

Drew Hirshfeld
*Performing the Functions and Duties of the*
*Under Secretary of Commerce for Intellectual Property and*
*Director of the United States Patent and Trademark Office*